US012665055B2

(12) United States Patent
Shanmuganathan et al.

(10) Patent No.: US 12,665,055 B2
(45) Date of Patent: Jun. 23, 2026

(54) DATA SECURITY FOR DATA SEQUENCES

(71) Applicant: Bedrock Labs, Inc., Menlo Park, CA (US)

(72) Inventors: Ganesha Shanmuganathan, San Jose, CA (US); Pranava Adduri, San Francisco, CA (US); Sohil Nizarali Habib, Cupertino, CA (US); Arun Soni, San Francisco, CA (US)

(73) Assignee: Bedrock Labs, Inc., Menlo Park, CA (US)

( * ) Notice: Subject to any disclaimer, the term of this patent is extended or adjusted under 35 U.S.C. 154(b) by 65 days.

(21) Appl. No.: 18/749,090

(22) Filed: Jun. 20, 2024

(65) Prior Publication Data

US 2025/0006310 A1      Jan. 2, 2025

Related U.S. Application Data

(60) Provisional application No. 63/524,502, filed on Jun. 30, 2023.

(51) Int. Cl.
*G16B 50/40*       (2019.01)
*G06F 21/60*       (2013.01)
*G16B 50/30*       (2019.01)

(52) U.S. Cl.
CPC ........... *G16B 50/40* (2019.02); *G06F 21/602* (2013.01); *G16B 50/30* (2019.02)

(58) Field of Classification Search
CPC ........ G16B 50/40; G16B 50/30; G06F 21/602
See application file for complete search history.

(56) References Cited

U.S. PATENT DOCUMENTS

| | | | | |
|---|---|---|---|---|
| 10,936,546 | B2 * | 3/2021 | Shanmuganathan | ... G06F 3/067 |
| 12,254,180 | B2 * | 3/2025 | Madan | ..... G06F 3/061 |
| 2017/0220289 | A1 * | 8/2017 | Arora | .... G06F 3/0604 |
| 2018/0052933 | A1 * | 2/2018 | Verma | ..... G06F 16/9535 |
| 2019/0220753 | A1 * | 7/2019 | Ramamurthy | ......... G06N 5/025 |
| 2019/0294800 | A1 * | 9/2019 | Andrews | ..... G06F 21/602 |
| 2024/0333746 | A1 * | 10/2024 | Williams | ..... H04L 51/02 |

FOREIGN PATENT DOCUMENTS

| | | | | |
|---|---|---|---|---|
| WO | WO-2022199864 | A1 * | 9/2022 | ..... H04L 9/003 |

OTHER PUBLICATIONS

Elworth (to Petabytes and beyond: recent advances in probabilistic and signal processing algorithms and their application to metagenomics, 2020 (Year: 2020).*

(Continued)

*Primary Examiner* — Linglan Edwards
*Assistant Examiner* — Jacob Benedict Knackstedt
(74) *Attorney, Agent, or Firm* — Van Pelt, Yi & James LLP

(57) ABSTRACT

Data security for data sequences is disclosed, including: receiving, over a network, a first sketch corresponding to a first file, wherein the first sketch was determined from hash values generated from a data sequence associated with the first file; determining that the first sketch and a second sketch corresponding to a second file at least partially overlap; and determining whether a data security policy is violated based at least in part on the determination that the first sketch and the second sketch at least partially overlap.

16 Claims, 16 Drawing Sheets

(56)                  References Cited

OTHER PUBLICATIONS

Baker et al., "Dashing: fast and accurate genomic distances with HyperLogLog." Genome biology 20 (2019): 1-12.

Elworth et al. "To petabytes and beyond: recent advances in probabilistic and signal processing algorithms and their application to metagenomics." Nucleic acids research 48.10 (2020): 5217-5234.

Katz et al. "STAT: a fast, scalable, MinHash-based k-mer tool to assess Sequence Read Archive next-generation sequence submissions." Genome Biology 22 (2021): 1-15.

Wikipedia, "HyperLogLog" accessed at https://en.wikipedia.org/wiki/HyperLogLog on Jun. 28, 2023.

Wikipedia, "Jaccard Index", accessed at https://en.wikipedia.org/wiki/Jaccard_index on Jun. 28, 2023.

Wikipedia, "Locality-sensitive hashing", accessed at https://en.wikipedia.org/wiki/Locality-sensitive_hashing on Jun. 28, 2023.

Xiaofei Zhao, "BinDash, software for fast genome distance estimation on a typical personal laptop." Bioinformatics 35.4 (2019): 671-673.

* cited by examiner

100

Sketch: {3, 9, 11}

Sketch: {7, 12, 29}

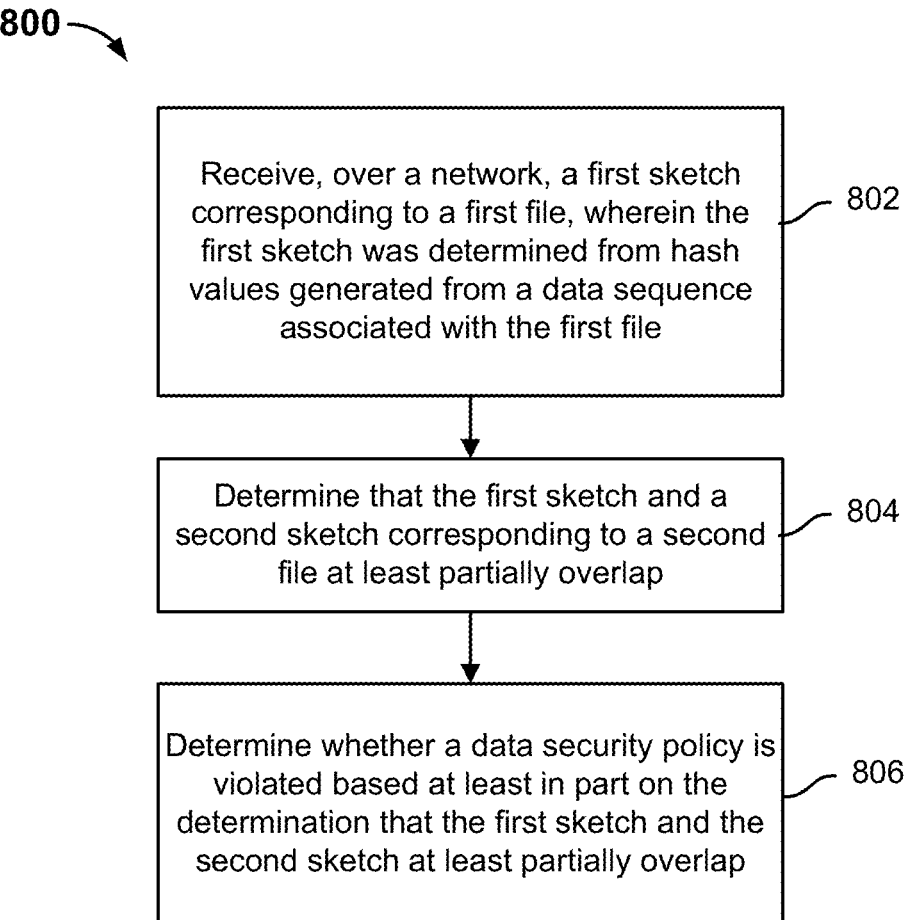

800

Receive, over a network, a first sketch corresponding to a first file, wherein the first sketch was determined from hash values generated from a data sequence associated with the first file ⟋ 802

Determine that the first sketch and a second sketch corresponding to a second file at least partially overlap ⟋ 804

Determine whether a data security policy is violated based at least in part on the determination that the first sketch and the second sketch at least partially overlap ⟋ 806

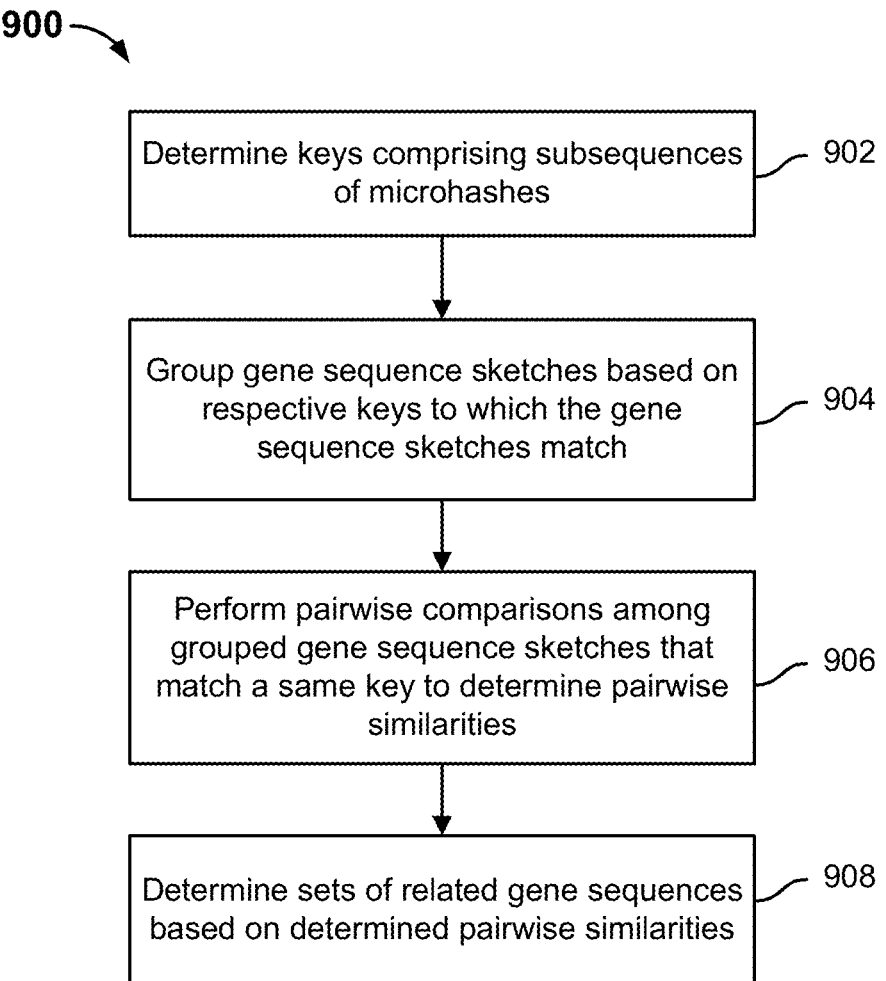

Determine keys comprising subsequences of microhashes — 902

Group gene sequence sketches based on respective keys to which the gene sequence sketches match — 904

Perform pairwise comparisons among grouped gene sequence sketches that match a same key to determine pairwise similarities — 906

Determine sets of related gene sequences based on determined pairwise similarities — 908

FIG. 9

Sketch1 = [3, 3, 15...]

Sketch2 = [3, 3, 80...]

Sketch3 = [3, 15, 70...]

1000

| Key | Value - Gene Sequence Sketches |
|---|---|
| [3, 3] | Sketch1, Sketch2 |
| [3, 15] | Sketch1, Sketch3 |
| [3, 80] | Sketch2 |
| ... | ... |

FIG. 10

Target: File1

1200 →

| Names of Related Gene Sequence Files | Similarity | Storage Location | Users with Access |
|---|---|---|---|
| File3 | 99.985 | LocationA | 20 principals |
| File2 | 99.984 | LocationB | 50 principals |
| File64 | 99.982 | LocationA | 20 principals |
| File36 | 99.981 | LocationA | 20 principals |
| File83 | 99.979 | LocationA | 20 principals |
| File29 | 99.974 | LocationB | 50 principals |

Start

Compare a current set of related gene sequence files to gene sequence data protection policies ⟍ 1302

Violation? ⟍ 1304

Yes

No

Send an alert and/or perform remediation to remove the violation ⟍ 1306

End

Sketch1 = [1, 3, 15...]

Sketch2 = [1, 3, 80...]

Sketch3 = [3, 57, 78...]

Sketch4 = [3, 4, 46...]

Sketch5 = [3, 22, 61...]

1500

| Key | Document Sequence Sketches |
|-----|----------------------------|
| 1 | Sketch1, Sketch2 |
| 2 | n/a |
| 3 | Sketch1, Sketch2, Sketch3, Sketch4, Sketch5 |
| 4 | Sketch4 |
| ... | ... |

DATA SECURITY FOR DATA SEQUENCES

CROSS REFERENCE TO OTHER APPLICATIONS

This application claims priority to U.S. Provisional Patent Application No. 63/524,502 entitled DATA SECURITY FOR GENOMICS DATA filed Jun. 30, 2023 which is incorporated herein by reference for all purposes.

BACKGROUND OF THE INVENTION

Sensitive files, such as those containing valuable intellectual property are monitored to ensure that derivatives are not made without permission. Examples of sensitive files include genomic data, text documents, and source code. However, traditional approaches for monitoring files, such as whole file hashing, face challenges when dealing with intellectual property. This is because even a minor alteration to the file containing intellectual property and/or its metadata could result in a change to the resulting hash value. As such, conventional comparison of whole-file hash values are unable to detect granular differences between the files and therefore, reliably detect when and how one file is similar to another file. It would be desirable to perform granular comparison of files in an efficient manner.

BRIEF DESCRIPTION OF THE DRAWINGS

Various embodiments of the invention are disclosed in the following detailed description and the accompanying drawings.

FIG. 8 is a flow diagram showing an embodiment of a process of enforcing data security on related data sequences.

FIG. 9 is a flow diagram showing an example process for determining pairwise similarities between gene sequence related sketches in accordance with some embodiments.

FIG. 10 is a diagram showing an example of grouping gene sequence sketches by matching keys in accordance with some embodiments.

FIG. 12 is a diagram showing a second visual representation of files whose representative sketches were determined to be similar in accordance with some embodiments.

FIG. 15 is a diagram showing an example of grouping data document sketches by matching keys in accordance with some embodiments.

DETAILED DESCRIPTION

Figure 1:
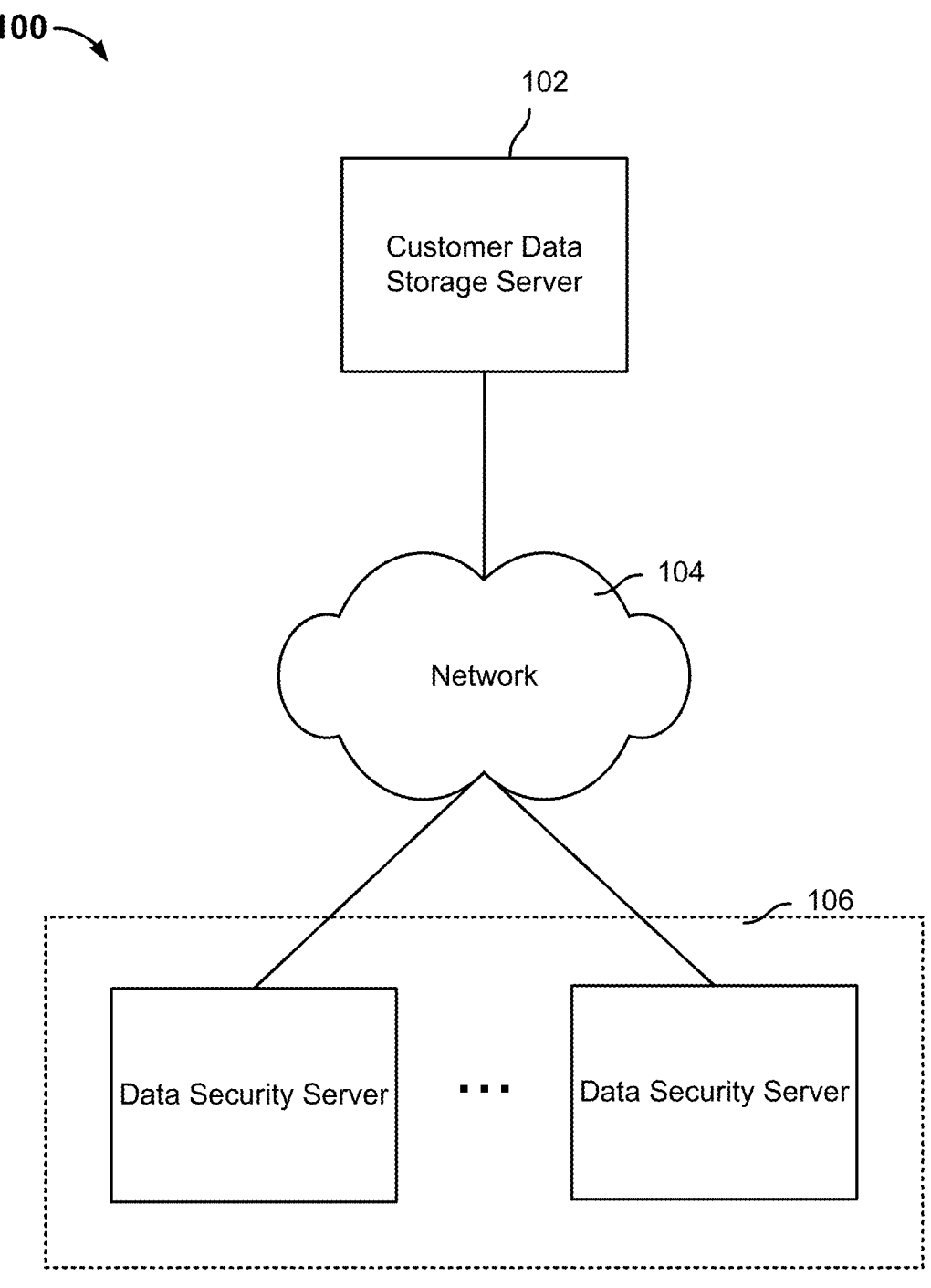
FIG. 1 is a diagram showing an embodiment of a system for ensuring data security of data sequences.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Embodiments of data security for data sequences are described herein. A first sketch corresponding to a first file is received over a network. The first sketch was determined from hash values generated from a data sequence associated with the first file. Examples of a first file include a data sequence such as a gene sequence, a text-based document, or a source code file. In some embodiments, the first sketch is derived from hash values generated from a partition from the data sequence (e.g., in the event that the entire data sequence exceeds a predetermined maximum size). An example of a partition of a gene sequence is a portion of the entire gene sequence. An example of a partition of a document file or a source code file is a linguistic unit such as a sentence, paragraph, page, or other logical unit. The first sketch is a lightweight representation of the first file's data sequence (or one or more partitions thereof). The first sketch and a second sketch are determined to at least partially overlap. The second sketch is a lightweight representation of a second file's data sequence (or one or more partitions thereof). In some embodiments, at least a portion of the first sketch and the second sketch overlapping indicates that the first file's data sequence (or one or more partitions thereof) and the second file's data sequence or one or more partitions thereof are similar to a corresponding degree. Whether a data protection policy is violated is determined based at least in part on the determination that the first sketch and the second sketch at least partially overlap. In some embodiments, given that the first file (or partition(s) thereof) and the second file (or partition(s) thereof) at least partially overlap, if such overlap violates a data protection policy, then an action is taken to remediate the violation.

As will be described below, comparing sketches that are derived from hash values calculated from (e.g., partitions of) the data sequences enable efficient and effective security monitoring and enforcement. The techniques described herein are particularly efficient because they reduce the amount of data that needs to be directly compared, allowing for quicker comparisons over large datasets. Additionally, the techniques are adaptable to various types of data, making it universally applicable across domains that handle sensitive or proprietary data sequences.

FIG. 1 is a diagram showing an embodiment of a system for ensuring data security of data sequences. System 100 includes customer data storage server 102, network 104, and multiple instances of data security server 106. Network 104 comprises data and/or telecommunications networks. Customer data storage server 102 and more than one instance of data security server 106 may communicate to each other over network 104. While only two instances of data security server 106 are shown in FIG. 1, in practice, more than two instances of data security server 106 can be operating in parallel to process the great volume of files associated with each data store in accordance with embodiments described herein. "Data security server 106" as used herein could encompass one or more instances of the server and its functionalities.

Customer data storage server 102 is configured to store data for a customer in one or more data stores. In various embodiments, customer data storage server 102 is configured to store files related to a customer (e.g., an institution or enterprise) of a party operating data security server 106. A first example of files stored at customer data storage server 102 includes sensitive files such as gene sequence files. Examples of file formats related to gene sequences includes file formats such as FASTA, FASTQ, SAM, and BAM. A second example of files stored at customer data storage server 102 includes documents with potentially sensitive data (e.g., tax information). Examples of file formats of documents include Microsoft Word®, Portable Document Format (PDF), and text files (TXT). A third example of files stored at customer data storage server 102 includes source code files with potentially sensitive data (e.g., proprietary code). Examples of file formats of source code files include .py and .cpp.

Files stored at customer data storage server 102 are desired to be compared to determine those that are meaningfully similar to each other to determine whether such relationships should exist in a data security context and if so, whether the related/similar files are currently similarly treated according to data security policies. However, given the potential sensitive nature of the files for which relatedness is to be determined and/or legal compliance with where sensitive information can be stored, the files stored at customer data storage server 102 are not to be transmitted as-is or in a form that can be used to recover the original file content away from customer data storage server 102. As such, in various embodiments, instead of transmitting the potentially sensitive files to be compared themselves from customer data storage server 102 to data security server 106, lightweight representations (which are also referred to as "sketches") related to the files are first determined at customer data storage server 102 and then the sketches are transmitted over network 104 to data security server 106. Sketching is a data summarization technique that approximates the original data using hashes of strategically chosen, representative samples of the underlying data. As will be described in further detail below, unlike traditional data security methods such as whole file hashing, the file-level sketches according to various embodiments described herein are generated such that minor or local changes within a file are not susceptible to the avalanche effect, which is when the resulting ciphertext representation of a file changes significantly even when the underlying data is only minorly changed. Data security server 106 could then evaluate the received sketches as reliable proxies for the files for which they represent to determine a granular degree of similarity, if any, among the represented files, as will be described in further detail below.

In various embodiments, depending on the type of files from which sketches are generated, data security server 106 may compare the sketches for degrees of similarity differently. In a first example, for gene sequence types of files, data security server 106 may determine the Jaccard similarity between two sketches derived from gene sequences. In a second example, for document types and source code types of files, data security server 106 may determine the count of common hashes within sketches that are determined from the documents/source code. Data security server 106 can then compare the determined degrees of similarities between two or more sketches to relatedness criteria to determine which sketches are "related." For the two or more sketches that are then determined to be similar enough to be "related" to each other, data security server 106 is configured to compare the meta information/configurations/settings of the files that are represented by the related sketches to data protection policies to determine whether any policy is violated. Examples of meta information of the files include the storage locations of the files and users/roles/applications or other types of access restrictions to the files. A first example of a data protection policy is if at least one file in a set of files with related sketches is stored in a sensitive storage location (e.g., with a given set of restrictions), then the related files should also be stored in the same storage location. A second example of a data protection policy is that a set of files whose sketches are related should have the same type of restrictions on access by users/applications. In the event that files that are represented by the related sketches violate a data protection policy, then data security server 106 is configured to perform an action. Examples of the action include to send an alert identifying the files and the policy that is violated to the device of a relevant user (e.g., to prompt the user to manually remediate the violation) or to programmatically remediate the violation (e.g., by increasing the access restrictions to one or more files).

Figure 2:
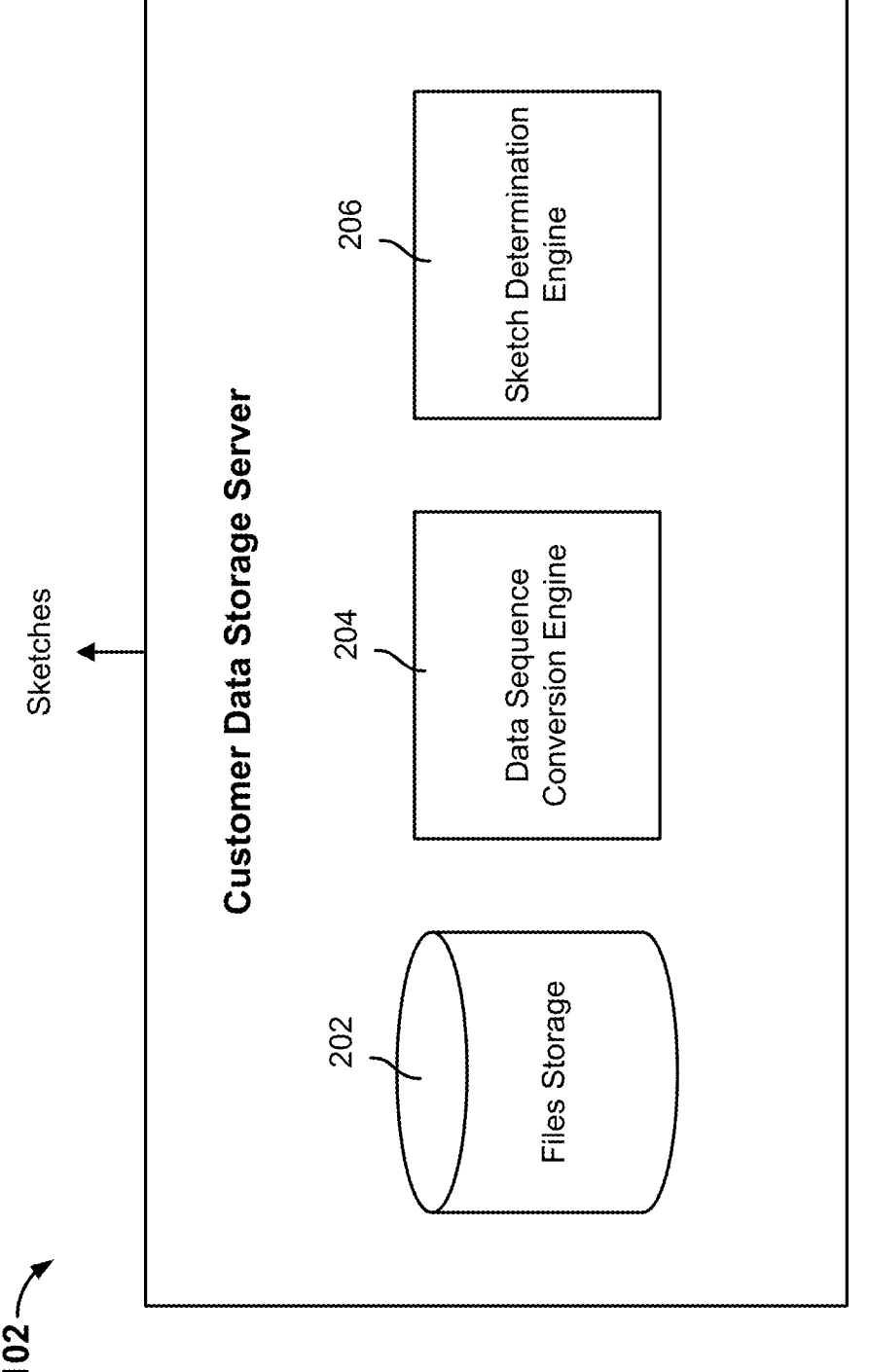
FIG. 2 is a diagram showing an example of a customer data storage server in accordance with some embodiments.

FIG. 2 is a diagram showing an example of a customer data storage server in accordance with some embodiments. In some embodiments, customer data storage server 102 of FIG. 1 may be implemented using the example customer data storage server of FIG. 2. As shown in FIG. 2, the example customer data storage server includes files storage 202, data sequence conversion engine 204, and sketch determination engine 206. Each of files storage 202, data sequence conversion engine 204, and sketch determination engine 206 may be implemented using hardware (comprising one or more processors) and/or software. In some embodiments, the example customer data storage of FIG. 2 is implemented by a cloud service for a particular customer.

Files storage 202 stores files of one or more types. For example, files storage 202 comprises one or more of structured, semi-structured, and unstructured data repositories. Specific examples of such data repositories include relational databases and/or data lakes. Examples of types of files that can be stored at files storage 202 include gene sequence files (e.g., including genetic sequences), text-based documents that are either structured (e.g., including fields, formatting, delineation, etc.) or unstructured, and/or source code. For example, at least some of the files stored at files storage 202 may be sensitive either due to including private or proprietary information. In particular, files storage 202 may store proprietary gene sequences that represent valuable intellectual property (e.g., trade secrets). Due to the potentially sensitive nature of files stored at files storage 202, it is desirable to monitor the usage, derivation, copying, and migration of such files to ensure that data protection policies are adhered to. Also, due to the potentially sensitive nature of such files and/or legal requirements for where certain data can be stored, it is undesirable to transmit the underlying data of the files stored at files storage 202 to a remote location for such monitoring.

In some embodiments, files storage 202 comprises one or more storage locations, where each storage location is associated with a set of access restrictions. In some embodiments, each file that is stored at files storage 202 is associated with metadata such as access restrictions to that file. Examples of access restrictions include one or more sets of users or roles that can access (e.g., read, write, delete, and/or update) a particular file or file(s) stored at a particular storage location.

Data sequence conversion engine 204 is configured to determine whether a file (e.g., that is stored in files storage 202) for which a sketch is to be generated (e.g., by sketch determination engine 206) should be first converted into a data sequence. In various embodiments, sketch determination engine 206 is configured to generate a sketch from a (e.g., unstructured) data sequence and as such, if the content of a file is not already in the form of a data sequence (e.g., does not meet data sequence criteria), data sequence conversion engine 204 is configured to convert the content into a data sequence. For example, if a file comprises a structured (e.g., with fields, columns, and/or rows) text-based document, then data sequence conversion engine 204 is configured to remove the structure/formatting from the text and then apply natural language processing (NPL) to standardize the text by, for example, removing stop words, changing tenses, etc. Put another way, data sequence conversion engine 204 is configured to convert the text-based content of a file into a standardized format associated with a data sequence. The resulting data sequence that is output by data sequence conversion engine 204 may be an unstructured stream (e.g., a long string) of text (e.g., characters). In some embodiments, the data sequences that are output by data sequence conversion engine 204 still preserve markers (e.g., periods, spacing) that delineate linguistic units within the text. Examples of linguistic units include sentences, paragraphs, and pages. In some embodiments, data sequence conversion engine 204 is configured to generate an abstract syntax tree from a source code file. In some embodiments, the abstract syntax tree can then be converted into a data sequence format. By generating an abstract syntax tree from the source code file, the resulting sketch(es) that are derived from the abstract syntax tree can be agnostic towards function name changes, variable name changes, and so forth.

Sketch determination engine 206 is configured to derive at least one sketch from a data sequence (e.g., that is derived by data sequence conversion engine 204) corresponding to a file (e.g., stored in files storage 202). In various embodiments, sketch determination engine 206 is configured to periodically scan files storage 202 for new files or updated files for which sketches have not yet been generated. In various embodiments, the data sequence that is directly obtained from a file or obtained by converting the contents of a file do not include the metadata associated with the file. In some embodiments, in the event that the data sequence exceeds a predetermined maximum size, sketch determination engine 206 is configured to divide the data sequence into one or more partitions. Otherwise, in the event that the data sequence does not exceed a predetermined maximum size, sketch determination engine 206 is configured to omit dividing the data sequence. Then, sketch determination engine 206 is configured to apply a sliding window (where the window has a length of k and so each set of characters within the sliding window is referred to as a "k-mer") to the data sequence (or partition thereof) and to generate a hash value (which is sometimes referred to as a "microhash") corresponding to each k-mer of the data sequence (or partition thereof). Examples of hash techniques that can be used to generate a microhash for each k-mer include Rabin Karp and cyclic hash. Sketch determination engine 206 is configured to, for the file's data sequence (or partitions thereof), sort the microhashes corresponding to the k-mers of the data sequence (or partitions thereof) and then select a subset of the smallest microhashes to use as a representative microhash selection or "sketch" for that data sequence (or each partition thereof). Depending on the type of the file, sketch determination engine 206 is configured to either directly send each sketch associated with the file with identifying information of the file (e.g., the filename and file type) over a network (not shown) to a data security server (e.g., data security server 106 of FIG. 1) for comparison to the sketches of other files, or combine (e.g., combine the microhashes from) one or more partition-level sketches derived from the file's data sequence into a sketch to represent that file and then send the file-level sketch over the network to the data security server for comparison to the file-level sketches of other files. In various embodiments, the metadata of a file is ignored by sketch determination engine 206 for the purpose of generating sketches.

In various embodiments, sketch determination engine 206 is configured to send sketches that represent files stored at files storage 202 over a network and not the underlying data of such files. In some embodiments, sketch determination engine 206 is configured to leverage a scanner (e.g., implemented using Go source text) to quickly process data and efficiently use serverless methods such as, for example, Amazon Web Services (AWS) Lambda, for massive parallel processing. This parallel processing architecture is combined with incremental scanning at user-tunable intervals, ensuring cost-efficient and continuous coverage of customers' data environments. In various embodiments, to efficiently monitor data and its derivatives at petabyte scale for usage, modification and movement, format aware data summarization techniques are leveraged. In some embodiments, sketch determination engine 206 provides an adapter architecture to summarize data sequences into sketches in a manner that is local to where the files corresponding to the data sequences are stored. Large partitions of the file's data sequence may be processed by sketch determination engine 206 in parallel using multiple computer processes (e.g., AWS Lambda workers), each of which will have multiple threads to compute microhashes in parallel.

The following describes a first example of sketch determination engine 206 generating sketches corresponding to a gene sequence type of file: Examples of gene sequence file formats include FASTA, FASTQ and SAM/BAM. Proprietary gene sequences represent valuable intellectual property, and as such, it is crucial to monitor the usage of such sequences and their derivatives during the genomic data analysis process. However, traditional approaches for monitoring files, such as whole file hashing, face challenges when dealing with gene sequence file formats. Alterations to these sequences frequently occur during genomic data analysis, such as trimming to remove low-quality reads, adding adapter sequences, and merging overlapping reads to generate longer contigs or scaffolds. Conventional genome analysis operations can substantially modify the metadata within these formats (e.g., annotations of coding/non-coding regions) as well as the fundamental sequences (e.g., merging multiple sequences into a single file). The alterations caused by these standard operations render traditional data security methods, like whole file hashing, ineffective due to their susceptibility to the avalanche effect, which is when even a minimally changed genomic data (e.g., the input to a hash function) can change the resulting ciphertext/hash. As such, in various embodiments, sketch determination engine 206 is configured to omit the metadata, which may change frequently and/or irrespective of the underlying gene sequence of a file, in these formats for computing sketches for gene sequence files. The metadata may be optionally processed separately as will be described later. For example, for FASTQ files, metadata such as quality scores are omitted and only the sequences therein are prepared to create sketches. Similarly, for example, for SAM/BAM files, metadata such as alignment information is omitted and only the sequences therein are prepared to create sketches. The resulting sequences, without metadata, are already data sequences (without conversion needed) and can now be optionally partitioned and hashed. In the context of gene sequences, if a file's gene sequence is larger/longer than a predetermined maximum size, then sketch determination engine 206 is configured to first divide the gene sequence into two or more partitions. Sketch determination engine 206 is configured to apply a k-length sliding window to each partition and hash the k characters within each window into a corresponding microhash value. Sketch determination engine 206 is configured to sort the microhashes generated for each partition (or undivided gene sequence) and select an N number of the smallest microhashes, where N is a configurable value. The N number of smallest microhashes can be placed into a data structure (e.g., array, vector) to serve as the sketch for that partition (or undivided gene sequence). Sketch determination engine 206 is configured to send each sketch that is associated with a partition (or undivided gene sequence) of a file with the filename and file type (and potentially other meta information such as which partition of the file the sketch is associated) over a network to the data security server for similarity comparisons to sketches related to other gene sequence files.

The following describes a second example of sketch determination engine 206 generating sketches corresponding to a document type of file: Examples of document types of file formats include Microsoft Word®, Microsoft Excel®, PDF, Rich Text, TXT, and EML. In various embodiments, sketch determination engine 206 is configured to omit the metadata in these formats for computing sketches for document files. The metadata may be processed separately, as will be described later, or ignored altogether. If a document file's content does not meet predetermined criteria associated with a data sequence, then data sequence conversion engine 204 is configured to convert the underlying data/content of the document into a data sequence that meets the predetermined criteria associated with a data sequence. Once the data sequence is available, in some embodiments, sketch determination engine 206 is configured to divide the document data sequence into partitions. In some embodiments, the partitions into which a document's data sequence is divided are linguistic units that are demarcated using punctuation (e.g., periods, carriage returns, page breaks, etc.) or other linguistic elements. Examples of linguistic units are sentences, paragraphs including one or more paragraphs, and pages. In some embodiments, sketch determination engine 206 is configured to omit dividing the document data sequence into partitions and consider the entire data sequence as a single linguistic unit for which to generate a corresponding sketch. Sketch determination engine 206 is configured to apply a k-length sliding window to each partition/linguistic unit and hash the k characters within each window into a corresponding microhash value. Sketch determination engine 206 is configured to sort the microhashes generated for each partition/linguistic unit and select an N number of the smallest microhashes, where N is a configurable value. The N number of smallest microhashes can be placed into a data structure (e.g., array, vector) to serve as the sketch for that partition/linguistic unit. In the example of a document type of file and where the data sequence was divided into two or more partitions, sketch determination engine 206 is configured to combine the respective sketches determined from the one or more partition/linguistic units into which the document data sequence was divided into a data structure (e.g., array, vector) to serve as the sketch for that entire document file. In the example of a document type of file and where the data sequence was not divided, sketch determination engine 206 is configured to determine a single sketch for that entire document file. Sketch determination engine 206 is configured to send the file-level sketch with the filename and file type over a network to the data security server for similarity comparisons to sketches related to other document files.

Figure 3:
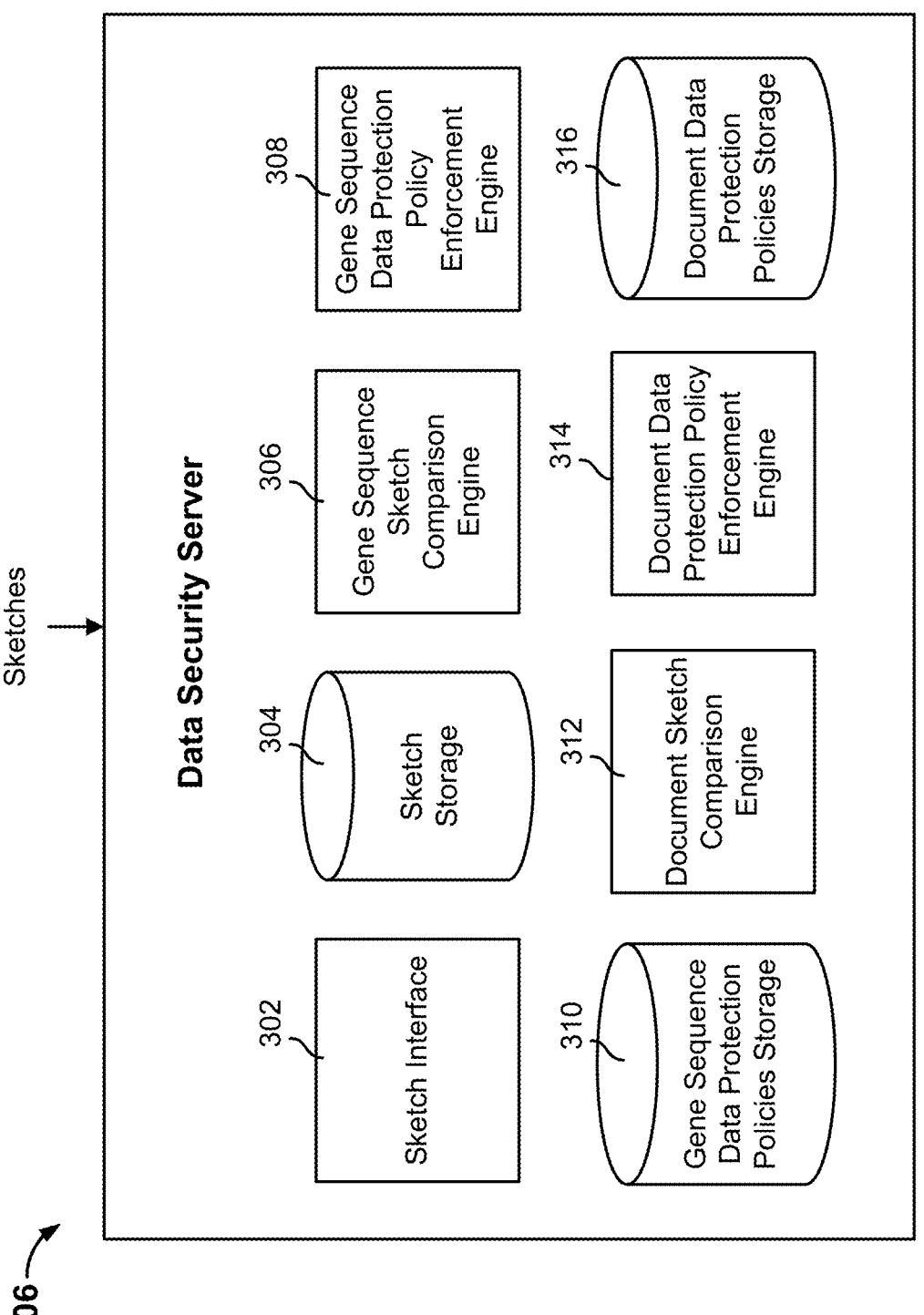
FIG. 3 is a diagram showing an example of a data security server in accordance with some embodiments.

FIG. 3 is a diagram showing an example of a data security server in accordance with some embodiments. In some embodiments, data security server 106 of FIG. 1 may be implemented using the example data security server of FIG. 3. As shown in FIG. 3, the example data security server includes sketch interface 302, sketch storage 304, gene sequence sketch comparison engine 306, gene sequence data protection policy enforcement engine 308, gene sequence data protection policies storage 310, document sketch comparison engine 312, document data protection policy enforcement engine 314, and document data protection policies storage 316. Each of sketch interface 302, sketch storage 304, gene sequence sketch comparison engine 306, gene sequence data protection policy enforcement engine 308, gene sequence data protection policies storage 310, document sketch comparison engine 312, document data protection policy enforcement engine 314, and document data protection policies storage 316 may be implemented using hardware (comprising one or more processors) and/or software.

Sketch interface 302 is configured to receive (e.g., over a network) sketches generated by one or more customer data storage servers (e.g., such as the example customer data storage server that is described in FIG. 2). In some embodiments, sketch interface 302 is configured to receive sketches associated with one or more types of files. For example, sketch interface 302 may receive sketches associated with gene sequence types, document types, and/or source code types of files. In various embodiments, each sketch that is received by sketch interface 302 includes file identifying information (e.g., a filename, partition identifying information, and a file type).

Sketch storage 304 is configured to store the sketches that are received (at sketch interface 302).

Gene sequence sketch comparison engine 306 is configured to compare sketches (e.g., stored at sketch storage 304) associated with gene sequence types of files to determine similarity between the sketches. As mentioned above, in some embodiments, a sketch that is derived from a gene sequence may be determined from either the entire, undivided gene sequence or a partition thereof. Because pairwise comparison among all pairs of gene sequence sketches that are stored at sketch storage 304 is very resource intensive, in some embodiments, gene sequence sketch comparison engine 306 is configured to first sort the gene sequence sketches into groups of potentially similar sketches and then perform pairwise comparisons among only gene sequence sketches that have been sorted into the same group. As will be described in further detail below, in some embodiments, gene sequence sketch comparison engine 306 is configured to sort gene sequence sketches that match (e.g., include) the same key comprising a small set of microhashes into a group of potentially similar sketches and then perform a more refined pairwise comparison (among the gene sequence sketches that have been sorted into the same key group to determine pairwise similarity values e.g., determining the Jaccard similarity) between pairs of gene sequence sketches. The same sketch can be matched to (e.g., stored as values in a key-value storage corresponding to) two or more keys. In some embodiments, gene sequence sketch comparison engine 306 is configured to cluster together gene sequence sketches whose similarity values meet or exceed a similarity threshold (e.g., 99%). Gene sequence sketches that are clustered together due to their similarity values meeting or exceeding the similarity threshold are sometimes referred to as being "related." As will be described in further detail below, two gene sequence sketches that are related indicate that the gene sequence (or partitions thereof) that they represent are themselves similar and that potentially, one of them is derived from the other. This approach for comparing gene sequences described herein accommodates variations inherent in genetic data processing, such as mutations or trimming in sequencing workflows.

Gene sequence data protection policy enforcement engine 308 is configured to evaluate clusters of gene sequence sketches that have been determined to be related (e.g., by gene sequence sketch comparison engine 306) against gene sequence data protection policies stored at gene sequence data protection policies storage 310. In some embodiments, gene sequence data protection policies storage 310 stores policies with which related gene sequences (or partitions thereof) should conform. For example, gene sequence data protection policies storage 310 may store default policies and also customized policies on the usage of gene sequences (e.g., allowed locations, exposure to subsidiaries, the similarity threshold for sending alerts). Given that a gene sequence (e.g., which describes the nucleotide makeup of an identified gene or an engineered gene) may be valuable intellectual property and/or private information, a first example gene sequence data protection policy may describe that all related gene sequences or gene sequences that are related to one or more target gene sequences must share the strongest access restrictions of any of the related gene sequences. A second example gene sequence data protection policy (a data boundary/perimeter type policy) may describe that all related gene sequences or gene sequences that are related to one or more target gene sequences must be stored in a specified storage location (e.g., associated with the strongest access restrictions). Gene sequence data protection policy enforcement engine 308 is configured to check the metadata/settings of the files of the related gene sequence sketches against the policies stored at gene sequence data protection policies storage 310. In some embodiments, gene sequence data protection policy enforcement engine 308 has previously obtained the metadata/settings of the files (e.g., entitlements (who can access what) as well as the access logs (who is accessing what)). Examples of the metadata/settings of the files of the related gene sequence sketches include a location at which each file is stored, which one or more users/roles can access the file, which permission(s) (e.g., read, write, delete, and update) each user or role is granted with respect to the file, etc. In the event that gene sequence data protection policy enforcement engine 308 determines that a set of related files (files that correspond to related gene sequence sketches) violates a gene sequence data protection policy, gene sequence data protection policy enforcement engine 308 is configured to perform a remediation action. A first example of a remediation action is to send an alert to a device associated with the customer to present at a user interface of the device identifying information of the files that violate the policy and a description of the violated policy. A second example of a remediation action is to modify the metadata/settings of one or more of the related files that had violated the policy such that the modified metadata/settings of the related files no longer violate the policy. Some specific examples of modifying the metadata/settings of a file is to move the file from an existing storage location to a new storage location (e.g., at which the files related to the first file are stored) and/or to change the access restrictions to the file to match the most restrictive permissions associated with a related file.

Document sketch comparison engine 312 is configured to compare sketches (e.g., stored at sketch storage 304) associated with document types and source code types of files to determine similarity between the sketches. As mentioned above, in some embodiments, a sketch that represents a document is a combination of sketches that have been determined for respective partitions/linguistic units into which the data sequence determined from the document's content was divided. In some embodiments, document sketch comparison engine 312 is configured to identify document-level sketches that match to a key comprising one or more microhashes and where each key represents a corresponding one or more linguistic units (e.g., one or more sentences). The same sketch can be matched to (e.g., stored as values in a key-value storage corresponding to) two or more keys. Put another way, two or more document-level sketches that match to the same key include/overlap by character subsequences that are represented by that key. In some embodiments, document sketch comparison engine 312 is configured to determine whether the document-level sketches that match the same key are "related" by comparing the count of document-level sketches to a set of related document criteria. For example, the related document criteria may describe that if more than a predetermined maximum of document-level sketches match to the same key, then the documents represented by those sketches may not necessarily be related (e.g., because the linguistic unit(s)

represented by that key are too commonplace and are not an indicator of whether documents that share them are meaningfully similar). Also, the related document criteria may describe if more than a predetermined minimum but fewer than the predetermined maximum of document-level sketches matches to the same key, then the documents represented by those sketches are "related" (e.g., because the common/overlapping character subsequences represented by that key are not too commonplace and therefore indicate that the documents are meaningfully similar). This approach for comparing data sequences described herein enables the detection of unauthorized copying or modifications of text across different documents/source code files.

Document data protection policy enforcement engine 314 is configured to evaluate related document-level sketches that have been determined to be related (e.g., by document sketch comparison engine 312) against document data protection policies stored at document data protection policies storage 316. In some embodiments, document data protection policies storage 316 stores policies with which related documents should conform. Given that a document may contain valuable intellectual property and/or private information, a first example document data protection policy may describe that all related documents must share the strongest access restrictions on any of the related documents. A second example document data protection policy (a data boundary/ perimeter type policy) may describe that all related documents or documents that are related to one or more target documents must be stored in a specified storage location (e.g., associated with the strongest access restrictions). Document data protection policy enforcement engine 314 is configured to check the metadata/settings of the files of the related document sketches against the policies stored at document data protection policies storage 316. Examples of the metadata/settings of the files of the related document sketches include a location at which each file is stored, which one or more users/roles can access the file, which permission(s) (e.g., read, write, delete, and update) each user or role has with respect to the file, etc. In the event that document data protection policy enforcement engine 314 determines that a set of related files (files that correspond to related documents) violates a document data protection policy, document data protection policy enforcement engine 314 is configured to perform a remediation action. A first example of a remediation action is to send an alert to a device associated with the customer to present at a user interface of the device identifying information of the files that violate the policy and a description of the violated policy. A second example of a remediation action is to modify the metadata/settings of one or more of the related files that had violated the policy such that the modified metadata/settings of the related files no longer violate the policy. Some specific examples of modifying the metadata/ settings of a file are to move the file to a new storage location (e.g., at which the files related to the first file are stored) and/or to change the access restrictions to the file to match the most restrictive permissions associated with a related file.

Figure 4:
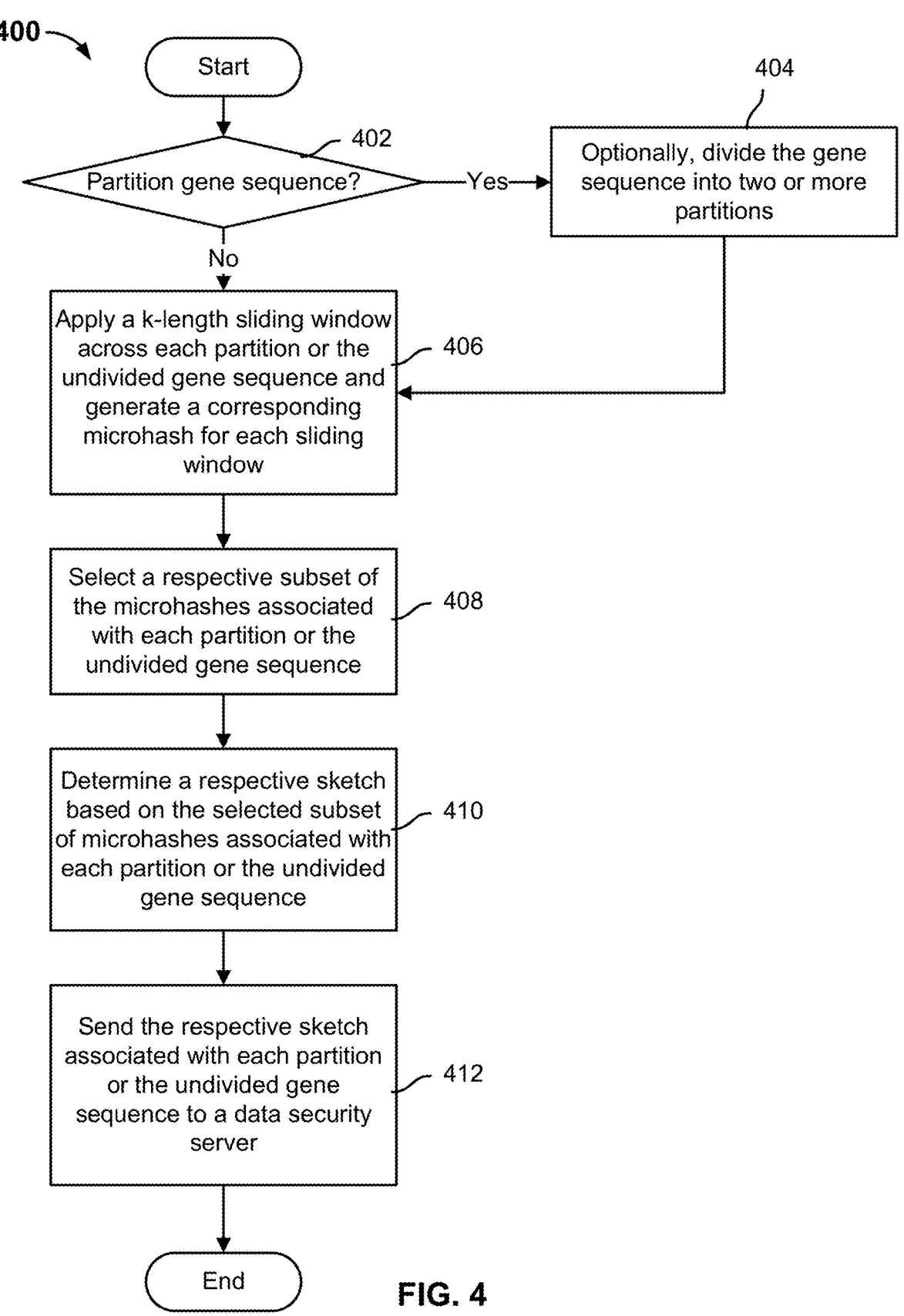
FIG. 4 is a flow diagram showing an example process of generating sketch(es) from a gene sequence in accordance with some embodiments.

FIG. 4 is a flow diagram showing an example process of generating sketch(es) from a gene sequence in accordance with some embodiments. In some embodiments, process 400 may be implemented, at least in part, on a customer data storage server such as customer data storage server 102 of FIG. 1.

At 402, whether a gene sequence from a gene sequence file should be partitioned is determined. The gene sequence comprising a nucleotide sequence is extracted from a gene sequence type file and the metadata (e.g., quality scores or annotations) are ignored. In the event that the gene sequence should be partitioned, control is transferred to 404. Otherwise, in the event that the gene sequence should not be partitioned, control is transferred to 406. For a gene sequence that is larger than a predetermined maximum length/size (e.g., 1024 MB), in some embodiments, the sequence is first divided into two or more partitions and a respective sketch (e.g., of a fixed length) is to be determined for each partition. Otherwise, if the gene sequence is not larger than the predetermined maximum length/size, then a single sketch (e.g., of a fixed length) is to be determined for the undivided gene sequence.

At 404, the gene sequence is, optionally, divided into two or more partitions. The larger than the predetermined maximum size gene sequence is optionally partitioned into two or more partitions. For example, the gene sequence is partitioned into partitions that are each no greater than 1 GB in size. In some embodiments, adjacent partitions can overlap by k characters, where k is the length of the sliding window, as will be described in more detail below.

At 406, a k-length sliding window is applied across each partition or the undivided gene sequence and corresponding microhash is generated for each k-length sliding window. A k-length sliding window is slid across each partition, if the gene sequence was divided, or if not, the k-length sliding window is slid across the entire gene sequence and a corresponding (e.g., fixed-length) microhash is determined for each sliding window by applying a given hash function to the adjacent characters (representing nucleotides) within each sliding window. Each sliding window with k characters can be referred to as a "k-mer." In some embodiments, k is selected to be 21 or greater based on recommendations from previous research. To compute the k-mers around the edge of a partition in case of large sequences, in some embodiments, the adjacent partitions can overlap by k so that the sliding window can be applied across the adjacent characters in the region of the sequence that was divided into two partitions.

At 408, a respective subset of the microhashes associated with each partition or the undivided gene sequence is selected.

At 410, a respective sketch is determined based on the selected subset of microhashes associated with each partition or the undivided gene sequence.

In various embodiments, the microhashes of each partition, if the gene sequence was divided, or if not, the microhashes of the entire gene sequence are sorted (e.g., from smallest to largest value), including any potential duplicate microhashes. Then, a subset of the smaller microhashes associated with each partition is selected, if the gene sequence was divided, or if not, a subset of the smaller microhashes associated with the entire gene sequence is selected.

In one example, the N number of smallest microhashes (including any duplicates) associated with each partition is selected for that particular partition, if the gene sequence was divided, or if not, the N number of smallest microhashes associated with the entire gene sequence is selected for that gene sequence. The selected subset of microhashes is included in a data structure (e.g., array, vector) to form the representative microhashes, or a sketch, of the gene sequence or partition thereof.

In another example, a MinHash sketch is used to select the subset of microhashes for the gene sequence or partition thereof:

Partition the range of possible microhash values into many bins.

Select the smallest microhash value in each bin as its representative.

If a bin is empty, choose the smallest microhash value from the next non-empty bin instead.

Generate a sketch by selecting a portion (e.g., the lowest b-bits) of each microhash value selected from the bins. Here, b-bits refer to the number of bits chosen from each microhash value to create a compact representation, with a smaller number of b-bits resulting in a more compressed representation and therefore, more microhashes can be stored using the same amount of storage space for the same sketch size. For example, b can be selected to be the lower 48 bits in a 64 bit hash. The selected portion (e.g., the lowest b-bits) of each bin's microhash value can be combined using a scheme to generate a resulting sketch for the gene sequence or partition thereof. For example, the selected microhash value portions are encoded using protobuf with variant encoding and then combined to create the sketch file associated with the gene sequence or partition thereof. The resulting sketch serves as a compact and approximate representation of the entire undivided gene sequence or partition thereof. The above example scheme uses the L-partition MinHash scheme. In other examples, min-L hashes can be used as an alternative hashing scheme.

At 412, the respective sketch associated with each partition or the undivided gene sequence is sent to a data security server. If the gene sequence were not partitioned, then the sketch that was determined for the entire undivided gene sequence is sent to the data security server. Otherwise, if the gene sequence were partitioned, then the sketch that was determined for each partition of the gene sequence is sent over a network to the data security server. For example, if the gene sequence were divided into two partitions, then two sketches corresponding to respective ones of the two partitions are both sent over a network to the data security server. In various embodiments, no underlying gene sequence data is ever sent to the data security server—only file identifying information (e.g., filenames, file types, and/or partition numbers) is sent with the sketches. The sketches are derived using one-way functions and cannot be reverse engineered (e.g., at the data security server) to recover the original genomic sequences. For a 5 GB sequence file, a sketch is estimated to be around 512 KB. The size of the sketch, for example, is controlled by the number of bins in the above algorithm. It is estimated that a 512 KB sketch for 5 GB worth of sequences should give enough resolution to find a 99.99% match (error less than 0.01%). As will be described in further detail below, at the data security server, the sketch(es) are to be compared against sketches associated with other gene sequences to determine whether the compared sketches are similar and therefore, their related gene sequences, are also similar.

Figure 5:
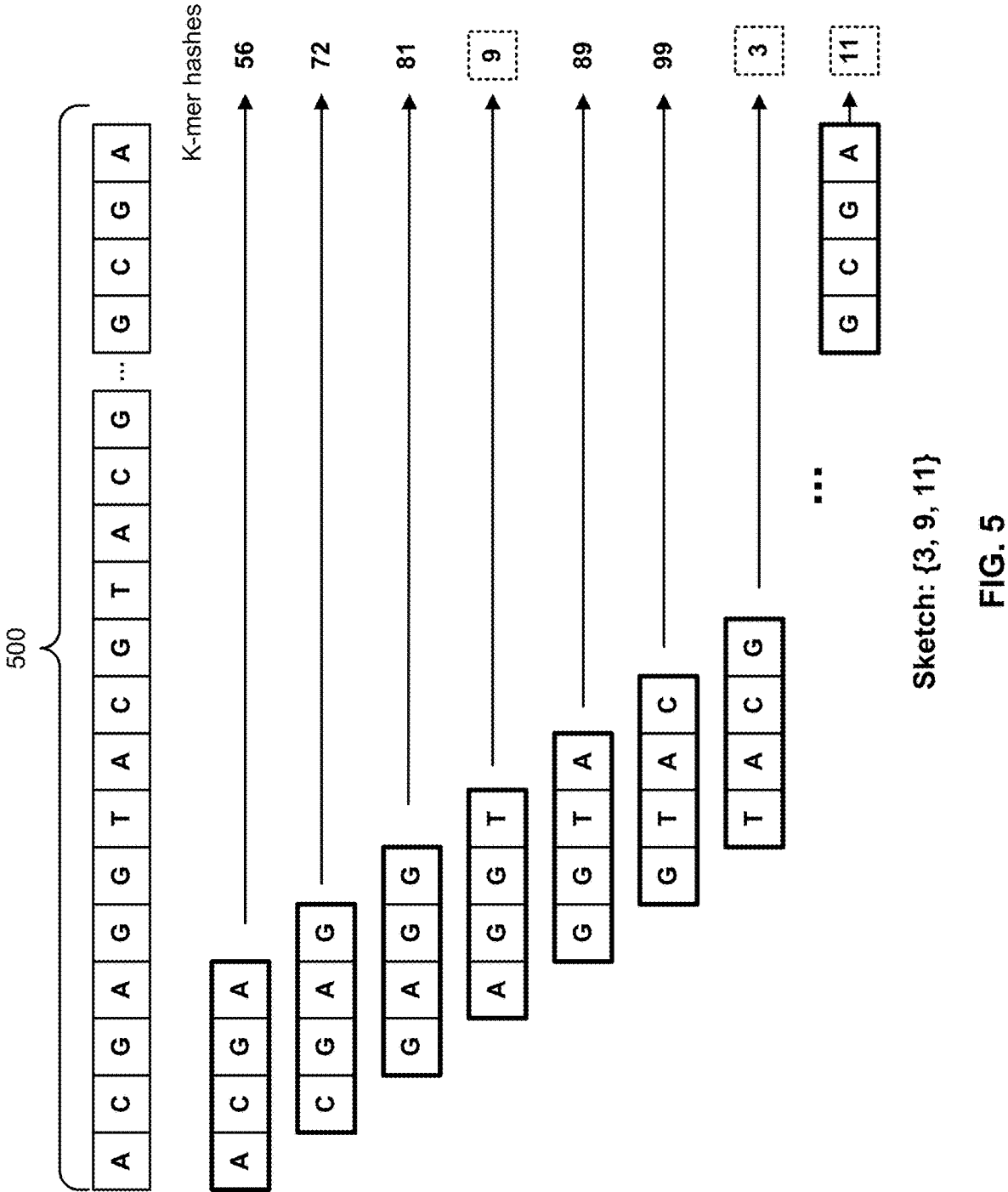
FIG. 5 is a diagram showing an example of generating a sketch from a gene sequence in accordance with some embodiments.

FIG. 5 is a diagram showing an example of generating a sketch from a gene sequence in accordance with some embodiments. Specifically, FIG. 5 describes generating a sketch corresponding to gene sequence 500 using a process such as process 400 of FIG. 4. In FIG. 5, gene sequence 500 is obtained from a gene sequence type file whose metadata is ignored for the purposes of generating a corresponding sketch. The length of gene sequence 500 is less than a threshold length and therefore, gene sequence 500 is not partitioned into two or more partitions. Gene sequence 500 comprises a series of characters, each representing a corresponding nucleotide ("A" for adenine, "G" for guanine, "T" for thymine, and "C" for cytosine), and forms a sequence that represents a gene or a portion thereof. To generate a lightweight sketch to represent gene sequence 500, a k-mer window is slid across gene sequence 500 and a hash function is applied to each consecutive k characters within the window to generate a corresponding k-mer microhash. In the example of FIG. 5, k=4. For example, the first k-mer of gene sequence 500 comprising ACGA has the microhash of 56, the second k-mer of gene sequence 500 comprising CGAG has the microhash of 72, the third k-mer of gene sequence 500 comprising GAGG has the microhash of 81, and so forth. After the corresponding microhash has been determined for each k-mer of gene sequence 500, in one example, the N smallest count of k-mer microhashes is selected and sorted by value to form the sketch to represent gene sequence 500. In the example of FIG. 5, N=3 and includes the three smallest k-mer microhashes shown in FIG. 5, which are 3, 9, and 11. As such, the sketch comprising [3, 9, 11] would represent gene sequence 500. The value of N can be tuned. Increasing the value of N would increase the accuracy of the comparison between gene sequence related sketches but would also increase the storage space needed to store such sketches. Decreasing the value of N would decrease the accuracy of the comparison between gene sequence related sketches but would also consume less the storage space for storing such sketches For example, each microhash if is 64 bits and each sketch included 1,000 microhashes, then the sketch would be 64 KB.

Figure 6:
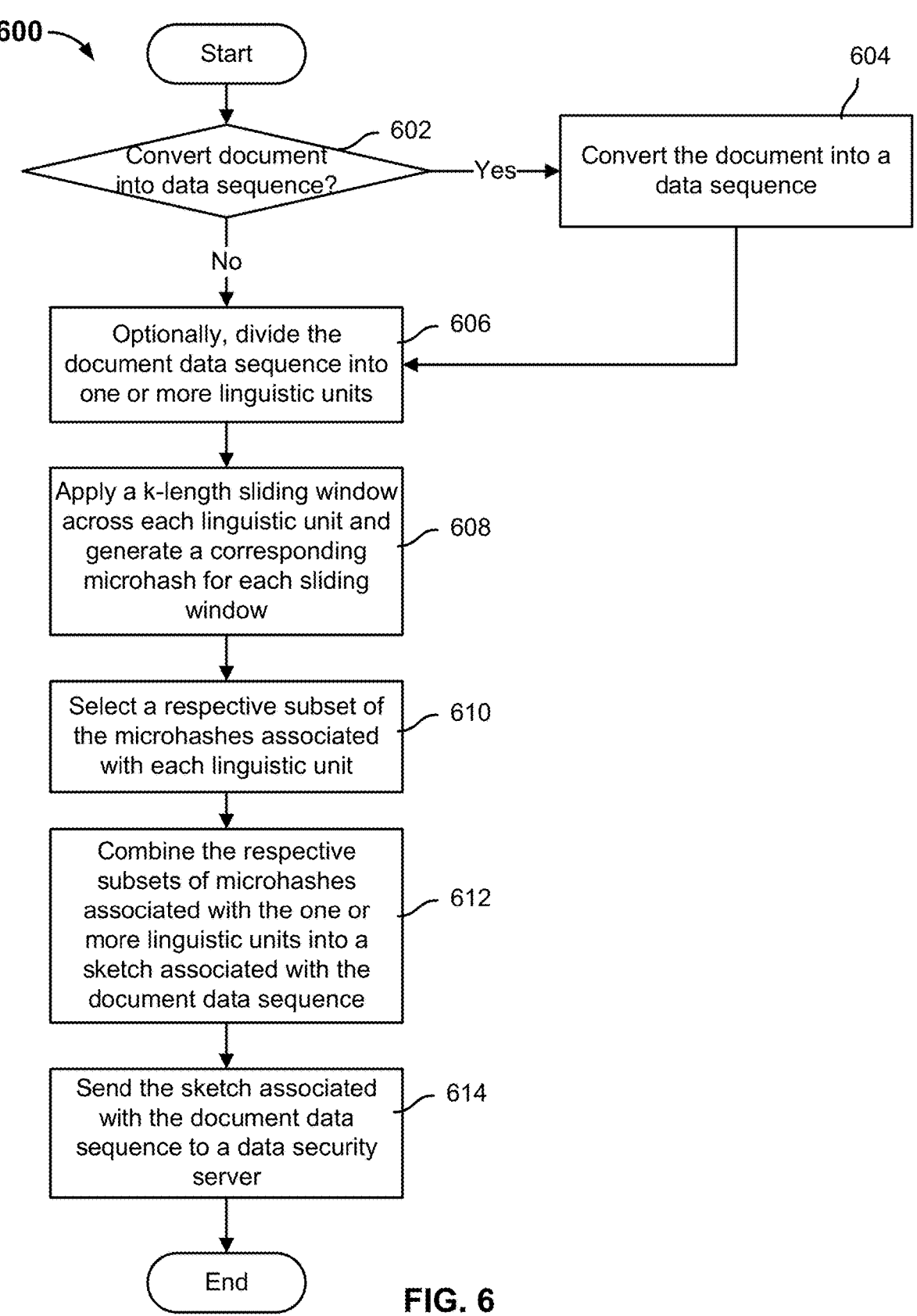
FIG. 6 is a flow diagram showing an example process of generating sketch(es) from a document in accordance with some embodiments.

FIG. 6 is a flow diagram showing an example process of generating sketch(es) from a document in accordance with some embodiments. In some embodiments, process 600 may be implemented, at least in part, on a customer data storage server such as customer data storage server 102 of FIG. 1.

In some embodiments, process 600 may be performed (e.g., as a background process on a regular interval) for each document or source code file that is determined from a storage. In some embodiments, process 600 may be performed in response to an event such as, for example, receiving an new document/message that is submitted by a user. For example, process 600 may be performed to generate a new sketch corresponding to a new document/ message that is submitted by a user and then a downstream sketch-based comparison process (e.g., process 1400 of FIG. 14) is performed based on the new sketch to determine whether the new sketch is related to the sketch of other (e.g., sensitive) document(s) and based on that determination, it can be determined whether the new message is permitted to be distributed. For example, if the new document/message is found to overlap with a sensitive document, then the new document/message may be prevented from being distributed to one or more recipients.

At 602, whether a document needs to be converted into a data sequence is determined. In the event that the document needs to be converted into a data sequence, control is transferred to 604. Otherwise, in the event that the document does not need to be converted into a data sequence, control is transferred to 606. In some embodiments, the text content is extracted from a document type file or the source code is extracted from a source code file and the metadata is ignored. The extracted text/source code content is compared to data sequence criteria, which describes the conditions of meeting a stream of text, and if the text content/source code content does not meet the data sequence criteria, then the text content/source code content is to be converted. For example, if the extracted text content includes structure (e.g., fields, columns, rows, delimiters, carriage returns), then the text content does not meet the data sequence criteria and needs to be converted into a data sequence. In another example, if the extracted source code is not already in a tree-structure, then the source code does not meet the data sequence criteria and needs to be converted into a data sequence.

At 604, the document is converted into a data sequence. For example, if the extracted text content comprises a structured (e.g., with fields, columns, and/or rows) text-based document, then the text content is processed to remove the structure/formatting from the text and then natural language processing (NPL) is applied to the text to remove stop words and change tenses, for example. The document's data is converted into a standardized data sequence format so that a representative sketch can be derived from the data sequence, as described below. If the extracted source code is not already in a tree-structure, then the source code is converted into an abstract syntax tree (e.g. that is converted into a data sequence format).

At 606, the document data sequence is optionally divided into one or more linguistic units. In some embodiments, whether the data sequence is divided into partitions is dependent on the size of the data sequence. In some embodiments, if the data sequence is greater than a predetermined maximum size, then the data sequence is divided into two or more partitions such as linguistic units (e.g., which are configurable to be sentences, paragraphs, pages). In some embodiments, if the data sequence is not greater than a predetermined maximum size, then the data sequence remains undivided and the entire data sequence can be considered to be a single linguistic unit.

At 608, a k-length sliding window is applied across each linguistic unit and a corresponding microhash is generated for each sliding window. A k-length sliding window is slid across each linguistic, and a corresponding (e.g., fixed-length) microhash is determined by applying a given hash function to the adjacent k characters (representing alphanumeric values) within each sliding window. Each sliding window with k characters can be referred to as a "k-mer." In some embodiments, k is selected to be 21 or greater based on recommendations from previous research.

At 610, a respective subset of the microhashes associated with each linguistic unit is selected.

In some embodiments, the microhashes of each linguistic unit are sorted (e.g., from smallest to largest value), including any potential duplicate microhashes. Then, a subset of the smaller microhashes associated with each linguistic unit is selected.

In order to ensure that microhashes are selected from different locations within a linguistic unit, in some embodiments, each linguistic unit is divided into spatial neighborhoods (e.g., where each spatial neighborhood is a contiguous set of characters). Then, microhashes that are generated from the sliding the k-length window across each a spatial neighborhood within the linguistic unit are associated with that particular spatial neighborhood. As such, to construct the sketch corresponding to the overall linguistic unit, in some embodiments, it is ensured that the smallest microhashes are selected from each spatial neighborhood within the linguistic unit. In some embodiments, the size of the spatial neighborhood is determined based on the overall size of the linguistic unit. For example, a larger linguistic unit will entail a larger spatial neighborhood and a smaller linguistic unit will entail a smaller spatial neighborhood.

In one example, the N number/count of smallest microhashes (including any duplicates) associated with each linguistic unit is selected for that particular linguistic unit. The selected subset of microhashes included in a data structure (e.g., array, vector) form the representative microhashes, or a sketch, of the data sequence or partition thereof. In some embodiments, MinHash is used to select the N number/count of smallest microhashes associated with each linguistic unit.

In yet another example, an L-partition MinHash sketch is used to select the subset of microhashes for each linguistic unit:

Partition the range of possible microhash values into many bins.

Select the smallest microhash value in each bin as its representative.

If a bin is empty, choose the smallest microhash value from the next non-empty bin instead.

Generate a sketch by selecting a portion (e.g., the lowest b-bits) of each microhash value selected from the bins. Here, b-bits refers to the number of bits chosen from each microhash value to create a compact representation, with a smaller number of b-bits resulting in a more compressed representation and therefore, more microhashes can be stored using the same amount of storage space for the same sketch size. For example, b can be selected to be the lower 48 bits in a 64-bit hash. The selected portion (e.g., the lowest b-bits) of each bin's microhash value can be combined using a scheme to generate a resulting sketch for the linguistic unit. For example, the selected microhash value portions are encoded using protobuf with variant encoding and then combined to create the sketch file associated with each linguistic unit. The resulting sketch serves as a compact and approximate representation of the linguistic unit. The above example scheme uses the L-partition Min-Hash scheme. In other examples, min-L hashes can be used as an alternative hashing scheme.

At 612, the respective subsets of microhashes associated with the one or more linguistic units are combined into a sketch associated with the document data sequence. In some embodiments, the linguistic unit level sketches associated with all the linguistic units of the file are combined into a document file-level sketch. Put another way, the microhashes included in the sketches that represent respective linguistic units of a document file's text content are merged to generate a single sketch that represents the file's text. However, if the linguistic unit is the entire data sequence, then the document file-level sketch is just the sketch determined for the single linguistic unit.

At 614, the sketch associated with the document data sequence is sent to a data security server. In various embodiments, no underlying document data is ever sent to the data security server-only file identifying information (e.g., filenames, file types) is sent with the sketch. The sketch is derived using one-way functions and cannot be reverse engineered (e.g., at the data security server) to recover the original documents. For a 5 GB sequence file, a sketch is estimated to be around 512 KB. The size of the sketch, for example, is controlled by the number of bins in the above algorithm. It is estimated that a 512 KB sketch for 5 GB worth of sequences should give enough resolution to find 99.99% match (error less than 0.01%). As will be described in further detail below, at the data security server, the sketch is to be compared against sketches associated with other documents to determine whether the compared sketches are similar and therefore, their related documents are also similar.

The example sketching technique described in process 600 is robust across longer sequences such as those found in FASTA files, as well as shorter sequences such as those found in FASTQ files.

Figure 7:
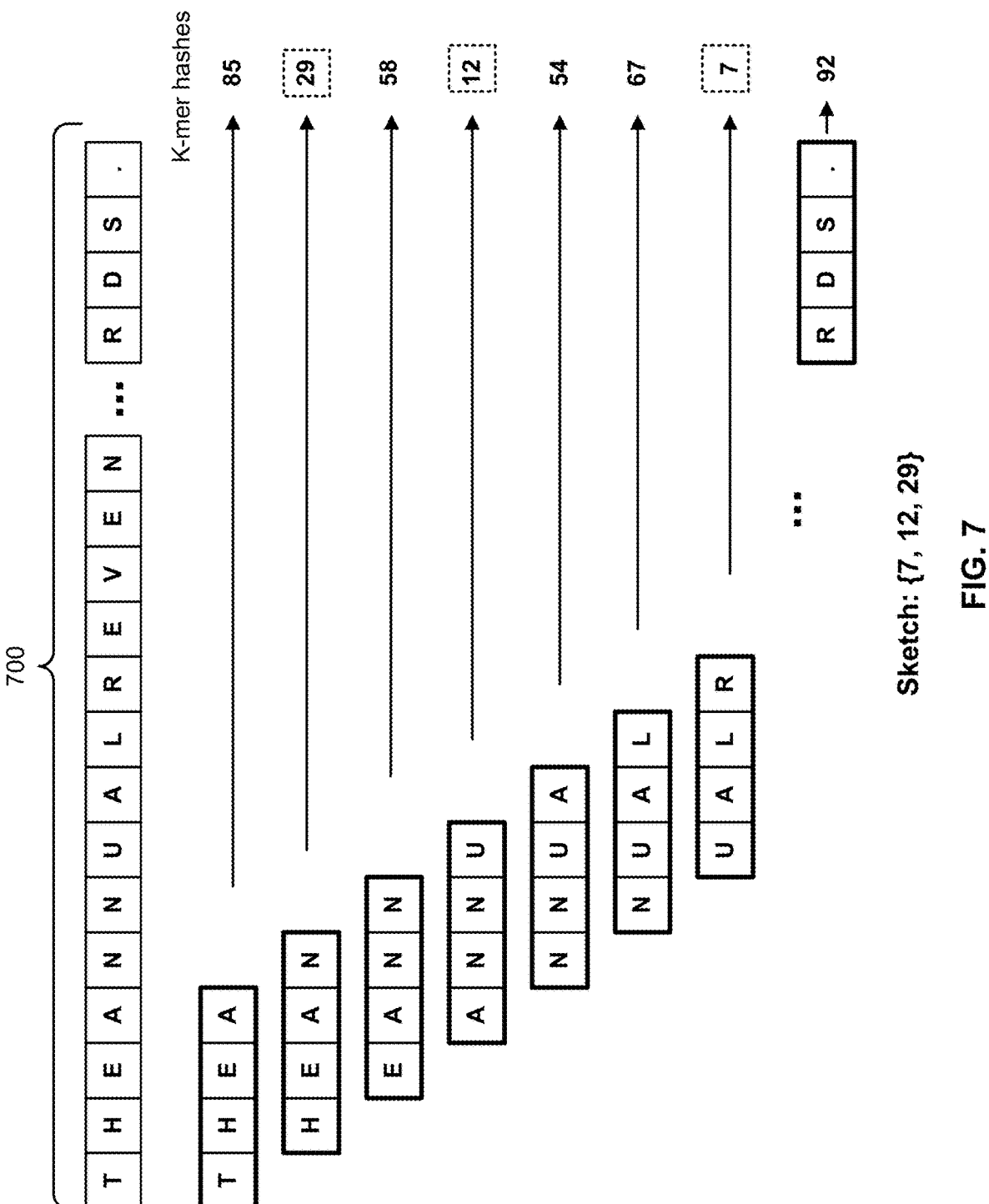
FIG. 7 is a diagram showing an example of generating a sketch from a linguistic unit in accordance with some embodiments.

FIG. 7 is a diagram showing an example of generating a sketch from a linguistic unit in accordance with some embodiments. Specifically, FIG. 7 describes generating a sketch corresponding to linguistic unit 700 using a process such as process 600 of FIG. 6. In FIG. 7, linguistic unit 700 comprises the entire data sequence that is obtained from a document type file whose metadata is ignored for the purpose of generating a corresponding sketch. Linguistic unit 700 is a sentence that comprises a series of characters, whose formatting has been processed and standardized to conform to the criteria for matching a data sequence. To generate a lightweight sketch to represent linguistic unit 700, a k-mer window is slid across linguistic unit 700 and a hash function is applied to each consecutive k characters within the window to generate a corresponding k-mer micro-hash. In the example of FIG. 7, k=4. For example, the first k-mer of linguistic unit 700 comprising THEA has the microhash of 85, the second k-mer of linguistic unit 700 comprising HEAN has the microhash of 29, the third k-mer of linguistic unit 700 comprising EANN has the microhash of 58, and so forth. After the corresponding microhash has been determined for each k-mer of linguistic unit 700, in one example, the N smallest count of k-mer microhashes is selected and sorted by value to form the sketch to represent linguistic unit 700. In the example of FIG. 7, N=3 and includes the three smallest k-mer microhashes shown in FIG. 7, which are 7, 12, and 29. The value of N can be tuned. Because in the example of FIG. 7 linguistic unit 700 comprises the entire data sequence of a document, sketch ({7, 12, 29}) forms the single sketch that represents that document file. Increasing the value of N would increase the accuracy of the comparison between document data sequence related sketches but would also increase the storage space needed to store such sketches. Decreasing the value of N would decrease the accuracy of the comparison between document data sequence related sketches but would also consume less storage space for storing such sketches.

FIG. 8 is a flow diagram showing an embodiment of a process of enforcing data security on related data sequences. In some embodiments, process 800 may be implemented, at least in part, on a data security server such as data security server 106 of FIG. 1.

At 802, a first sketch corresponding to a first file is received over a network, wherein the first sketch was determined from hash values generated a data sequence associated with the first file. In some embodiments, the first file comprises a gene sequence type file or a document type file. In various embodiments, the first sketch that corresponds to and represents the underlying data of the first file is generated at and obtained from a customer data storage server. In some embodiments, the first sketch corresponding to the first file is generated using a process such as process 400 of FIG. 4 if the file is a gene sequence type file or using a process such as process 800 of FIG. 8 if the file is a document type or source code type file. The first sketch comprises hash values (e.g., microhashes) that are determined from (e.g., a set of one or more partitions associated with) the data sequence of the file.

At 804, the first sketch and a second sketch corresponding to a second file are determined to at least partially overlap. The first sketch is compared to a second sketch that is derived from a second file of the same file type as the first file as proxies for the comparing the first file to the second file. In various embodiments, a degree of similarity is determined between the first sketch and the second sketch based on the amount of overlap, if any, that exists between the two sketches. The first and/or second sketch can be compared not only to each other but other sketches derived from other files as well. One advantage of comparing the sketches derived from the first and second files instead of comparing the two files themselves is that the sketches are much smaller than the files they represent and so the comparison of sketches is more computationally efficient than the comparison of files. Another advantage of comparing the sketches derived from the first and second files instead of comparing the two files themselves is that the files themselves may contain sensitive information that may not be desirable (or compliant with regulations) to transmit over a network or transmit from their original storage location unlike the sketches, which cannot be used to recover the sensitive information of the files.

At 806, whether a data protection policy is violated is determined based at least in part on the determination that the first sketch and the second sketch at least partially overlap. If the degree of similarity/overlap between the first sketch and the second sketch meets a set of relatedness criteria, then the first and second files that are represented respectively by the first and second sketches are determined to be "related" and therefore, should be compared against one or more data protection policies. In various embodiments, a data protection policy prescribes requirements to which related files should conform. For example, a data protection policy describes that related files should share similar or the same types of access restrictions. In the event that the first and second files violate a data protection policy, an action is performed. Examples of actions include to send an alert to a user device and/or to programmatically modify a setting of the file and/or second files to remediate the violation.

FIG. 9 is a flow diagram showing an example process for determining pairwise similarities between gene sequence related sketches in accordance with some embodiments. In some embodiments, process 900 may be implemented, at least in part, on a data security server such as data security server 106 of FIG. 1. In some embodiments, steps 802 and 804 of process 800 of FIG. 8 may be implemented, at least in part, using process 900.

Gene sequence related sketches, which are sketches that are each derived from either a gene sequence or a partition thereof using a process such as process 400 of FIG. 4, that are received at the data security server are to be compared against each other. In the context of comparing gene sequence sketches, it is desired to detect gene sequences with high similarities to (e.g., that share unique genetic components with) each other and label those as being "related." This is because a strong similarity between gene sequences is a meaningful indicator that, potentially, one of the gene sequences was derived from the other, which would then trigger the need to treat the related gene sequences with the same security measures/protections. However, the computation costs associated with performing pairwise comparisons between every pair of gene sequence sketches is high $(O(n^2))$ and so it is desirable to reduce the number of pairwise comparisons that need to be performed. Process 900 describes an example process of first grouping together sketches that match a key (and therefore have a higher probability of being related (e.g., sufficiently similar) to each other) and then only computing pairwise comparisons between the two or more sketches that are within the same group.

At 902, keys comprising subsequences of microhashes are determined. In some embodiments, each key comprises a subsequence of M microhashes. In some embodiments, M is selected based on the size of the gene sequence sketch and/or other factors. In some embodiments, the keys are determined by applying an M-sized sliding window across each gene sequence related sketch (e.g., which are each derived from either a gene sequence or a partition thereof using a process such as process 400 of FIG. 4) that are to be compared against other such sketches and then each unique subsequence of microhashes that is included in the M-sized sliding window is selected to be a key.

At 904, gene sequence sketches are grouped based on respective keys to which the gene sequence sketches match. Each gene sequence sketch is compared to each key to determine which gene sequence sketch(es) include that key and therefore matches to that key. A gene sequence sketch may include more than one key and therefore match to several keys. In one implementation, the sketches that match to a key are stored as the value in a key-value storage. In this way, gene sequence sketch(es) that match the same key belong to the same group.

In another example, locality-sensitive hashing (LSH) can be used to group gene sequence sketches and then pairwise comparisons are performed on the gene sequence sketches of the same group.

At 906, pairwise comparisons among grouped gene sequence sketches that match a same key are performed to determine pairwise comparisons. Pairwise comparisons are compared among gene sequence sketch(es) that match the same key. Gene sequence sketches that match the same key/belong in the same group are considered to at least share the subsequence of microhashes associated with the key and due to this preliminary determination of overlap, the more computationally expensive pairwise comparisons are then performed on these grouped sketches. In various embodiments, pairwise comparisons are not performed on sketches that do not match to the same key on the consideration that they will be unlikely to be related (e.g., sufficiently similar) to each other. In some embodiments, to determine the pairwise similarity between a pair of gene sequence sketches that match the same key, the Jaccard similarity coefficient is computed. The Jaccard similarity is a measure that quantifies the similarity between two sets by calculating the ratio of the number of elements they have in common (the intersection) to the total number of distinct elements in both sets (the union). In this context, the Jaccard similarity is the ratio between the size of the intersection of the (e.g., count of common) microhashes in the pair of sketches divided by the size of the union (e.g., the total count of all) of the microhashes across the pair of sketches.

At 908, sets of related gene sequences are determined based on determined pairwise similarities. The gene sequence sketches whose pairwise similarities (e.g., Jaccard similarity coefficients) with each other meet a set of relatedness criteria (e.g., including meeting a threshold Jaccard similarity coefficient) are determined to be "related" to each other and therefore, belong to the same cluster. As a result, the gene sequences or their partitions thereof that are represented by the related gene sequence sketches are also determined to be related and therefore, belong to the same cluster. For example, gene sequences whose respective sketches have Jaccard similarity coefficients greater than 99.5% can be determined to be related. In some embodiments, the set of relatedness criteria (e.g., including meeting a threshold Jaccard similarity coefficient) is configurable and different sets of relatedness criteria may be configured for different gene sequence file formats (e.g., FASTA, FASTQ, SAM, and BAM). As will be described below, related gene sequences should receive similar treatment and therefore will be compared against data protection policies to determine whether their current configurations and settings violate any policies.

FIG. 10 is a diagram showing an example of grouping gene sequence sketches by matching keys in accordance with some embodiments. In FIG. 10, process 900 of FIG. 9 is used to match gene sequence sketches identified by Sketch1, Sketch2, and Sketch3, each comprising a sorted series of microhashes, to respective keys. In the example of FIG. 10, keys are determined as a unique pair of microhashes that were determined by applying a two microhash-length sliding window across at least each of Sketch1, Sketch2, and Sketch3. Some of the keys that were determined by sliding this two microhash-length sliding window across each of Sketch1, Sketch2, and Sketch3 include [3, 3], [3, 15], and [3, 80]. Each of Sketch1, Sketch2, and Sketch3 is then compared to each of key [3, 3], [3, 15], and [3, 80] to determine which sketches include which subsequences. Each sketch that includes the two-microhash subsequence of a key is then stored as part of the value corresponding to the key. As shown in FIG. 10, table 1000 stores for each key, identifying information associated with the one or more sketches that matched to that key. If more than one sketch matched to a key, then those sketches are considered to overlap and can be grouped together for the next step of performing pairwise comparisons. Similarly, pairwise comparisons are not performed for sketches that do not match to the same key. Referring back to table 1000, because Sketch1 and Sketch2 both match key [3, 3], a pairwise comparison is performed across the microhashes of the two sketches to determine a degree of similarity (e.g., the Jaccard similarity coefficient) between the pair of sketches. Furthermore, because Sketch1 and Sketch3 both match key [3, 15], a pairwise comparison is performed across the microhashes of the two sketches to determine a degree of similarity (e.g., the Jaccard similarity coefficient) between the pair of sketches. Lastly, because Sketch2 and Sketch3 do not match to a same key (i.e., do not overlap a two-microhash subsequence that forms a key) in the example of FIG. 10, a pairwise comparison will not be performed across the microhashes of the two sketches to determine a degree of similarity. In some embodiments, gene sequence sketches whose pairwise similarities (e.g., Jaccard similarity coefficients) with each other meet a set of relatedness criteria (e.g., including meeting a threshold Jaccard similarity coefficient) are determined to be "related" to each other and therefore, belong to the same cluster.

Figure 11:
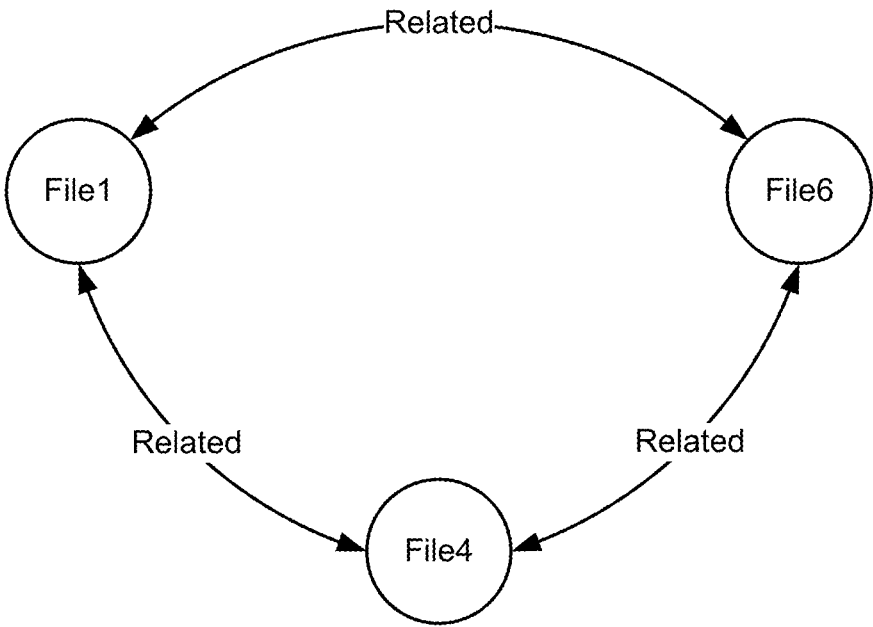
FIG. 11 is a diagram showing a first visual representation of files whose representative sketches were determined to be similar in accordance with some embodiments.

FIG. 11 is a diagram showing a first visual representation of files whose representative sketches were determined to be similar in accordance with some embodiments. Gene sequence type files that include gene sequences (or partitions thereof) whose representative sketches were determined to be sufficiently similar and therefore "related" are then themselves considered to be "related." The "related" relationships among files can be visually presented. In the example visual representation that is shown in FIG. 11, gene sequences files File1, File4, and File6 are determined to be "related" after the pairwise similarities were determined based on their associated sketches. In FIG. 11, each file is visually represented as a node labeled with its filename and an edge connects pairs of files that are determined to be related. In this example, each of File1, File4, and File6 is determined to be related to the other two.

FIG. 12 is a diagram showing a second visual representation of files whose representative sketches were determined to be similar in accordance with some embodiments. Gene sequence type files that include gene sequences (or partitions thereof) whose representative sketches were determined to be sufficiently similar to a target gene sequence type file's representative sketch are then themselves considered to be "related" to the target file. In the example visual representation that is shown in FIG. 12, for a given target file (e.g., a file that is of interest or significance), File1, each file whose related representative sketches were determined to be similar to (e.g., have a Jaccard similarity coefficient relative to) File1's representative sketch by over the threshold of 99.9 is determined to be similar to File1. Each file related to File1 is sorted from the most similar (e.g., having the highest Jaccard similarity coefficient relative to File1's representative sketch) to the least. FIG. 12 shows an example user interface at which a target gene sequence file, File1, is presented with table 1200 of related gene sequence files, starting with the most similar file, File3 with a 99.985% similarity, to the least similar file, File29 with a 99.974% similarity. Each entry in table 1200 pertaining to a file that is related to target File1 also includes additional information, such as the file's Jaccard similarity coefficient relative to File1's sketch, the location on storage (e.g., at the customer data storage server) at which the file is stored, and identifying information associated with users that currently have access to that file. The example presentation that is shown in FIG. 12 describes a lineage of related files relative to a particular target file (File1). For example, from this presentation, it can be inferred that File3, which is the most similar to File1, may have been directly derived from File1, and that File2, which is the second most similar to File1, may have also been directly derived from File or potentially, File3, and so forth. As will be described below, meta information associated with related files (e.g., storage location and users with access) may be compared against data protection policies to ensure that such configurations of related files do not violate the policies.

Figure 13:
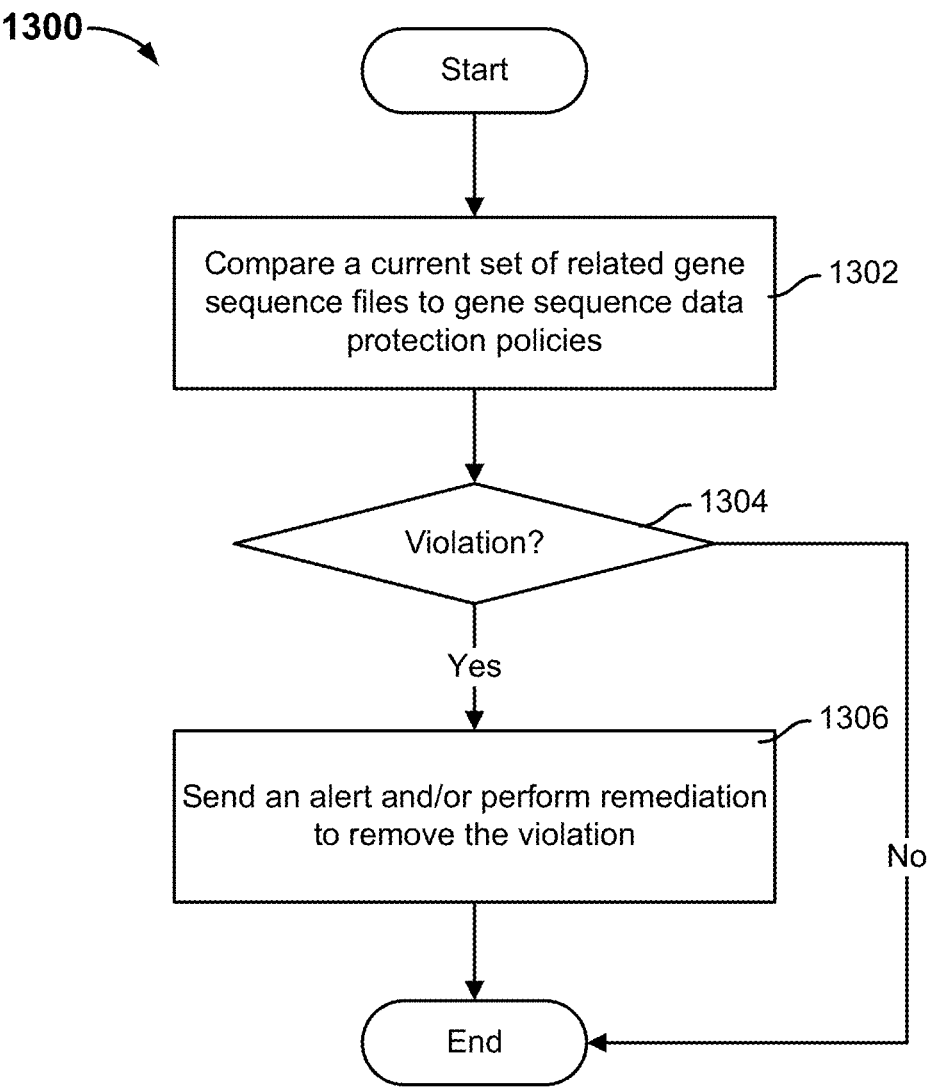
FIG. 13 is a flow diagram showing an example of a process of comparing related data sequence files against gene sequence data protection policies in accordance with some embodiments.

FIG. 13 is a flow diagram showing an example of a process of comparing related data sequence files against gene sequence data protection policies in accordance with some embodiments. In some embodiments, process 1300 may be implemented, at least in part, on a data security server such as data security server 106 of FIG. 1. In some embodiments, step 806 of process 800 of FIG. 8 may be implemented, at least in part, using process 1300.

At 1302, a current set of related gene sequence files is compared to gene sequence data protection policies. In various embodiments, gene sequences of gene sequence type files are periodically checked for whether they are related based on representative sketches. For example, whether gene sequences of gene sequence type files are related can be determined using a process such as process 900 of FIG. 9.

In various embodiments, the data security server provides a comprehensive suite of gene sequence data protection policies that effectively safeguard sensitive data. For example, the data protection policies may be default and/or configured by customers.

One example data protection policy allows users to set specific parameters, such as "Data related to that under path x in bucket b should not exist outside authorized paths." Put another way, an example data protection policy could identify a target (e.g., highly sensitive, patented) file and designate that all files related to the target file should only be stored in a target location (e.g., an authorized path). In a specific example, gene sequences that are related to a designated (e.g., highly sensitive) gene sequence should not leave the production environment. Another example data protection policy specifies the set of users/roles (e.g., administrators and principals) and/or the types of access (e.g., write, read, modify, and/or delete) that are permitted to be configured for related gene sequence files or gene sequence files that are related to a target (e.g., highly sensitive) file. Yet another data protection policy can check whether personally identifiable information (PII) and/or protected health information (PHI) is presented within the gene sequence files' metadata and send an alert if a policy is set to find those. In some embodiments, at least some of the data protection policies may prescribe an action if the specified conditions are not met by related gene sequence files.

In some embodiments, the data protection policies can be customized based on a user's environment, data accessibility, and the number of permitted copies. In some embodiments, the data protection policies allow users to specify the degree of similarity to look for along with where and how the similar files can exist (e.g., as specified by account, bucket, or tags). In some embodiments, the data security server can also allow users to tag environments and datastores.

At 1304, whether any of the data protection policies are violated by the current set of related gene sequence files is determined. In the event that at least one data protection policy is violated by the current set of related gene sequence files, control is transferred to 1306. Otherwise, in the event that none of the data protection policies are violated by the current set of related gene sequence files, process 1300 ends. In various embodiments, the current meta information and/or configurations of related gene sequence files are compared to the data protection policies to determine whether any of the policies are violated (e.g., not conformed to).

At 1306, an alert is sent and/or remediation to remove the violation is performed. If a policy is violated, an action that is prescribed by the policy can be performed. For example, the prescribed action may be to send an alert to a user device and in which the alert describes the file(s) that violated the policy and the policy that was violated. In another example, the prescribed action may be to modify a configuration/setting of one or more related files. In a first specific example, if gene sequence files are related to a target, and sensitive gene sequence files are not stored at a designated location (e.g., meant for sensitive data) that is prescribed in the policy, then the related gene sequence files can be programmatically migrated to the designated location. In a second specific example, if gene sequence files are related to a target, and sensitive gene sequence files are accessible by non-administrative users, then the access to the related files may be programmatically modified to only allow administrative users to access those files.

In some embodiments, which users and/or their roles that can access related gene sequences files and are actually accessing them are tracked and such actions may violate a data protection policy, which may lead to an action (e.g., an alert being sent to a user device).

Example process 1300 provides monitoring capability that allows the data security server to detect policy violations, such as, for example, when a patented gene subsequence is moved to a subsidiary account without appropriate attribution or protective measures.

Once the genomic file adapter is built, the data security server can serve as an automatic sequence catalog and can cluster similar sequences, enabling taxonomy use cases. Users can also quickly search for overlapping sequences in the data security server's console and find related sequences by varying the percentage of overlap. Users do not need to do anything other than store sequences as they normally would—the data security platform will discover, catalog, and categorize sequences programmatically.

The data security platform can also help with identifying batch effects such as sequence contamination from the human genome. These metagenomic checks can be done automatically and can be queried from the platform's catalog.

The above scheme may not detect two sequences as different if their only difference is a large-scale genome rearrangement, such as chromosome duplication. To address this issue, alternative methods like HyperLogLog or HULK could be used. Nevertheless, L-Partition MinHash is used in some embodiments because, from a data security perspective, it is more important to focus on identifying and alerting when derived sequences are found. A sequence that is only different in rearrangement is most likely a derived sequence.

Figure 14:
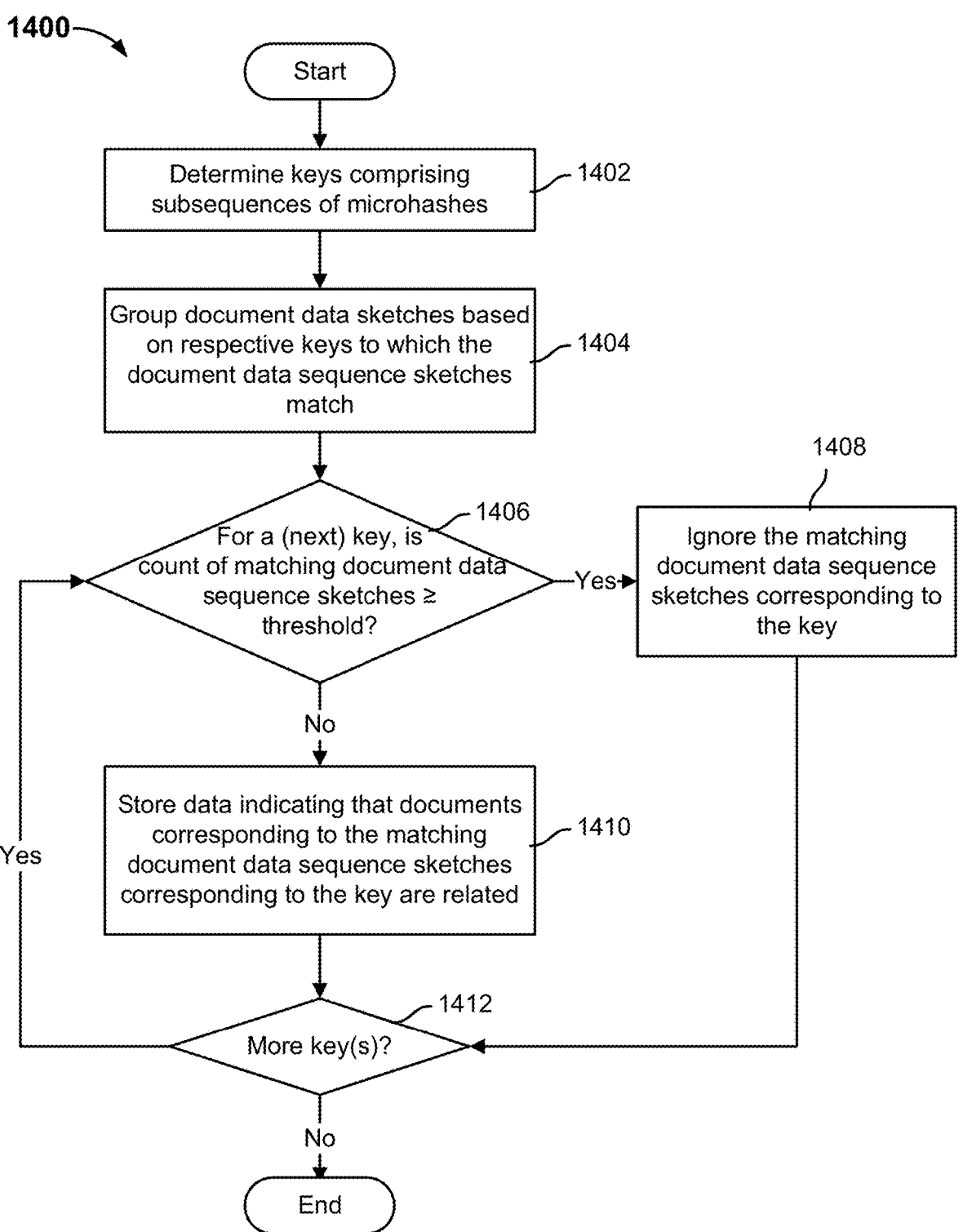
FIG. 14 is a flow diagram showing an example of a process of grouping document data sequence related sketches in accordance with some embodiments.

FIG. 14 is a flow diagram showing an example of a process of grouping document data sequence related sketches in accordance with some embodiments. In some embodiments, process 1400 may be implemented, at least in part, on a data security server such as data security server 106 of FIG. 1. In some embodiments, steps 802 and 804 of process 800 of FIG. 8 may be implemented, at least in part, using process 1400.

Document data related sketches, which are sketches that are each derived from a document's data sequence using a process such as process 600 of FIG. 6, that are received at the data security server are to be compared against each other. In the context of comparing document data sequences sketches, it is desired to detect document data sequences with overlapping one or more linguistic units and potentially label those as being "related" so long as the overlapping linguistic units are not themselves common (e.g., appearing within more than a threshold count of documents). This is because the overlap of one or more uncommon linguistic units is a meaningful indicator that, potentially, one of the documents had copied a portion of (e.g., potentially sensitive) text from the other, which would then trigger the need to treat the related documents with the same security measures/protections.

At 1402, keys comprising subsequences of microhashes are determined. In some embodiments, each key comprises a subsequence of M microhashes. In some embodiments, M is one microhash. In some embodiments, the keys comprise the unique microhashes that have been included in any sketch that has been generated for a document/source code using a process such as process 600 of FIG. 6.

At 1404, document data sketches are grouped based on respective keys to which the document data sequence sketches match. Each document data sequence sketch is compared to each key to determine which document data sequence sketch(es) include that key and therefore match to that key. A document data sequence sketch may include more than one key and therefore match to several keys. In some implementations, the sketches that match to a key are stored as the value in a key-value storage. In this way, document data sequence sketch(es) that match the same key belong to the same group. In the context of document comparison, when more than one document data sequence sketch matches a key, it means that the document files that correspond to those document data sequence sketches all include the character subsequence that is represented by that matching key.

In another example, locality-sensitive hashing (LSH) can be used to group document data sequence sketches and then pairwise comparisons are performed on the document data sequence sketches of the same group.

At 1406, for a (next) key, whether a corresponding count of matching document data sequence sketches is equal to or greater than a threshold count is determined. In the event that the corresponding count of matching document data sequence sketches is equal or greater than a threshold count, control is transferred to 1408. Otherwise, in the event that the corresponding count of matching document data sequence sketches is less than the threshold count, control is transferred to 1410.

As mentioned above, in various embodiments, it is of interest when more than one document data sequence sketch matches to the same key (e.g., includes the same character subsequence), but only if the key is not commonly appearing. For example, a non-sensitive series of words (e.g., a common disclaimer, an introduction) may appear in multiple documents but its presence among the documents, on its own, should not warrant a data security action. Based on intuition, it is presumed that a character subsequence that is represented by a key that appears in fewer than a threshold count of document files (absent other factors) is perhaps uncommon/potentially sensitive and that therefore, should trigger a data protection policy enforcement. Similarly, it is presumed that a character subsequence that is represented by a key that appears in more than at least a threshold count of document files (absent other factors) is perhaps common/non-sensitive and that therefore, should not trigger a data protection policy enforcement. As such, it is determined whether more than at least a threshold count of document data sequence sketches (that represent as many document files) match to the same key (i.e., all include the character subsequence that is represented by that key) and therefore should not, on that basis alone, be considered to be related. In some embodiments, this threshold count is configurable and can be increased or decreased to tune the sensitivity of document overlap detection. For example, the threshold of documents may be 10. In some embodiments, a reverse map of microhash to document sketch count can be maintained such that if a microhash is determined to belong to more than a threshold count of document sketches (e.g., according to the reverse map), then the microhash may be ignored for the purposes of determining related documents.

At 1408, the matching document data sequence sketches corresponding to the key are ignored. Where there are more than at least the threshold count of documents that match to the same key (i.e., all include the character subsequence that is represented by that key), then this particular key does not cause the group of represented document files to be considered as being related to each other. In this way, the keys that match to more than the at least threshold count of document data sequence sketches are filtered out from being the basis of the represented documents being considered to be related.

At 1410, data indicating that documents corresponding to the matching document data sequence sketches corresponding to the key are related is stored. Where there are fewer than the threshold count of documents that match to the same key (i.e., all include the character subsequence that is represented by that key), then this particular key does cause the group of represented document files to be considered as being related to each other. In this way, the keys that match to fewer than the threshold count of document data sequence sketches are presumed to be meaningful overlaps of (e.g., uncommon) portions of text among documents, which should cause the overlapping documents to be "related."

At 1412, whether there is at least one more key for which a count of matching data sequence sketches are to be evaluated is determined. In the event that there is at least one more key for which a count of matching data sequence sketches are to be evaluated, control is returned to 1406. Otherwise, in the event that there are no more keys for which a count of matching data sequence sketches are to be evaluated, process 1400 ends.

Unlike the gene sequence context which seeks to find significant (e.g., 90% or above) similarity between gene sequence file related sketches before deeming the files to be "related," in the document context, document file related sketches need only overlap at least one (e.g., uncommon) linguistic unit related sketch to be considered "related."

FIG. 15 is a diagram showing an example of grouping data document sketches by matching keys in accordance with some embodiments. In FIG. 15, process 1400 of FIG. 14 is used to match document data sequence sketches identified by Sketch1, Sketch2, Sketch3, Sketch4, and Sketch5 each comprising a series of microhashes, to respective keys. In the example of FIG. 15, each key is a unique microhash (e.g., that has appeared in any of the generated document data sequence sketches and) that represents a corresponding character subsequence. The keys include microhashes [1], [2], [3], and [4]. Each sketch that includes the single microhash of a key is then stored as part of the value corresponding to the key. As shown in FIG. 15, table 1500 stores for each key, identifying information associated with the one or more document file related sketches that matched to that key. If more than one sketch matched to a key, then those sketches are considered to overlap and can be grouped together for the next step of determining whether more than a threshold count of sketches match to that key. In the example of FIG. 15, the threshold count is three. Referring back to table 1500, because less than the threshold count of three sketches (Sketch1 and Sketch2) match key [1], overlapping Sketch1 and Sketch2 are considered to be related based on the overlap of key [1]. Furthermore, because more than the threshold count of three sketches (Sketch1, Sketch2, Sketch3, Sketch4, and Sketch5) match key [3], overlapping Sketch1, Sketch2, Sketch3, Sketch4, and Sketch5 are not considered to be related based on the overlap of key [3].

In some embodiments, document data sketches that are determined to be "related" to each other belong to the same cluster.

Figure 16:
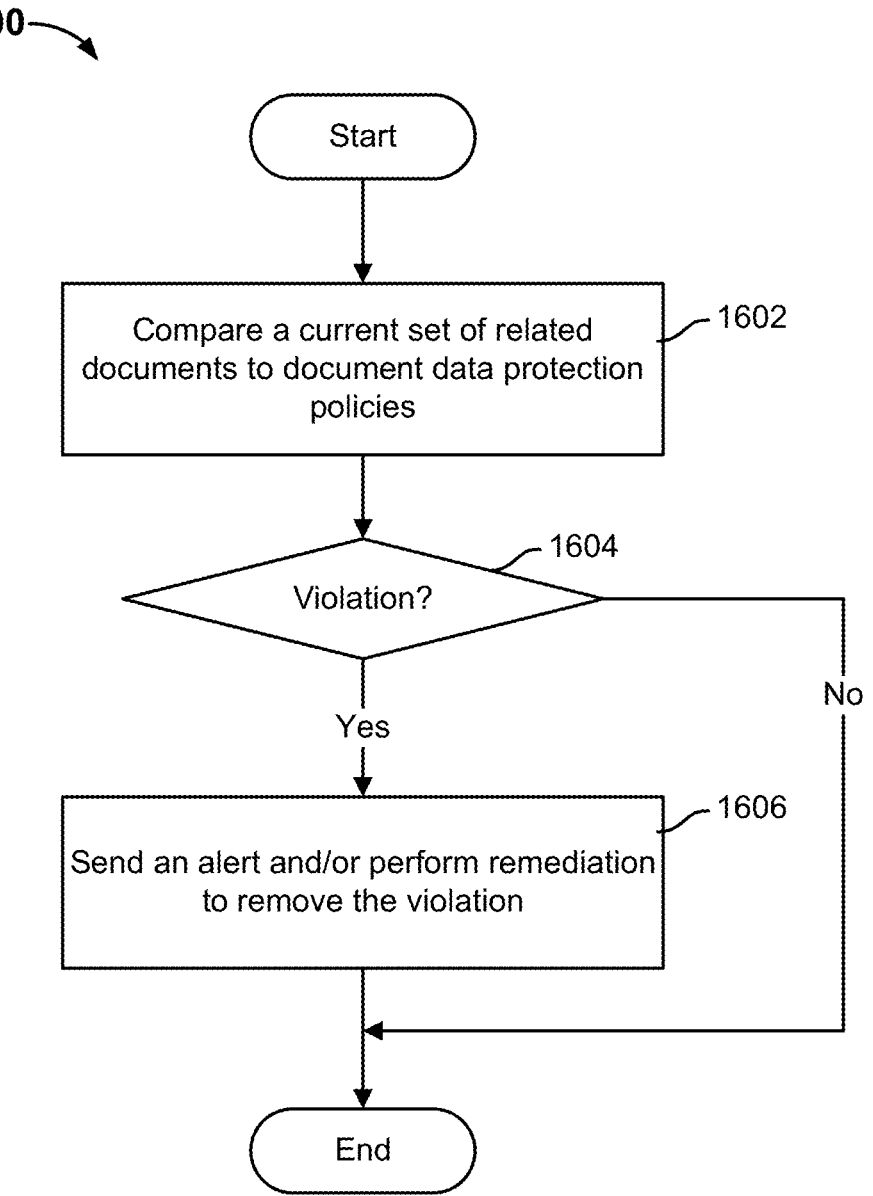
FIG. 16 is a flow diagram showing an example of a process of comparing related data sequence files against document data protection policies in accordance with some embodiments.

FIG. 16 is a flow diagram showing an example of a process of comparing related data sequence files against document data protection policies in accordance with some embodiments. In some embodiments, process 1600 may be implemented, at least in part, on a data security server such as data security server 106 of FIG. 1. In some embodiments, step 806 of process 800 of FIG. 8 may be implemented, at least in part, using process 1600.

At 1602, a current set of related document files are compared to document data protection policies. In various embodiments, document content of document type files are periodically checked for whether they are related based on representative sketches. For example, whether document content of document type files are related can be determined using a process such as process 1400 of FIG. 14.

In various embodiments, the data security server provides a comprehensive suite of document data protection policies that effectively safeguard sensitive data. For example, the data protection policies may be default and/or configured by customers.

One example data protection policy allows users to set specific parameters, such as "Data related to that under path x in bucket b should not exist outside authorized paths." Put another way, an example data protection policy could identify a target (e.g., highly sensitive) file and designate that all files related to the target file should only be stored in a target location (e.g., an authorized path). In a specific example, documents that are related to a designated (e.g., highly sensitive) document should not leave the production environment. Another example data protection policy specifies the set of users/roles (e.g., administrators and principals) and/or the types of access (e.g., write, read, modify, and/or delete) that are permitted to be configured for related document files or document files that are related to a target (e.g., highly sensitive) file. Yet another data protection policy can check whether personally identifiable information (PII) and protected health information (PHI) are present in the document files' metadata and send an alert if a policy is set to find those. In some embodiments, at least some of the data protection policies may prescribe an action if the specified conditions are not met by related document files.

In some embodiments, the data protection policies can be customized based on a user's environment, data accessibility, and the number of permitted copies. In some embodiments, the data protection policies allow users to specify the degree of similarity to look for along with where and how the similar files can exist (e.g., as specified by account, bucket, or tags). In some embodiments, the data security server can also allow users to tag environments and datastores.

At 1604, whether any of the data protection policies are violated by the current set of related document files is determined. In the event that at least one data protection policy is violated by the current set of related document files, control is transferred to 1606. Otherwise, in the event that none of the data protection policies are violated by the current set of related document files, process 1600 ends. In various embodiments, the current meta information and/or configurations of related document files are compared to the data protection policies to determine whether any of the policies are violated (e.g., not conformed to).

At 1606, an alert is sent and/or remediation to remove the violation is performed. If a policy is violated, an action that is prescribed by the policy can be performed. For example, the prescribed action may be to send an alert to a user device and in which the alert describes the file(s) that violated the policy and the policy that was violated. In another example, the prescribed action may be to modify a configuration/setting of one or more related files. In a first specific example, if document files are related to a target and/or sensitive document files are not stored at a designated location (e.g., meant for sensitive data) that is prescribed in the policy, then the related document files can be programmatically migrated to the designated location. In a second specific example, if document files are related to a target and/or sensitive document files are accessible by non-administrative users, then the access to the related files may be programmatically modified to only allow administrative users to access those files.

In some embodiments, which users and/or their roles that can access related document/source code files and are actually accessing them are tracked and such actions may violate a data protection policy, which may lead to an action (e.g., an alert being sent to a user device).

In various embodiments, scanning and generating sketches from incoming files can be performed in real-time or periodically (e.g., the process can run every night and only scan files that were created during that day) at the customer data storage server. The file scanning can be performed in a parallelized manner and terabytes of data can be scanned in minutes. With 250 parallelized computer processes (e.g., AWS Lambdas) running in parallel in tests, files can be processed at 12.5 GB/s. With 500 parallelized computer processes, files can be processed at 25 GB/s and so on. The data security server can send alerts in minutes based on the policies that are configured.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
first one or more processors configured to:
    apply a k-length sliding window to a linguistic unit associated with a document data sequence to generate a corresponding hash value for each sliding window, wherein the document data sequence is associated with a first file;
    select a respective subset of hash values associated with the linguistic unit;
    determine a first sketch associated with the document data sequence based at least in part on the respective subset of hash values associated with the linguistic unit; and
    send the first sketch associated with the document data sequence over a network;
a sketch interface configured to receive, over the network, the first sketch corresponding to the first file; and
second one or more processors configured to:
    determine that the first sketch and a second sketch corresponding to a second file at least partially overlap, wherein to determine that the first sketch and the second sketch corresponding to the second file at least partially overlap comprises to:
        determine keys comprising subsequences of hash values;
        group the first sketch and the second sketch based on the first sketch and the second sketch both matching a key:
        determine whether a count of matching sketches to the key meets or is greater than a threshold count; and
        in response to a determination that the count of the matching sketches to the key does not meet or exceed the threshold count, determine that the first sketch and the second sketch are related; and
    in response to a determination that a data security policy is violated based at least in part on the determination that the first sketch and the second sketch at least partially overlap, modify a security setting associated with the first file.

2. The system of claim 1, wherein the first file comprises a document file.

3. The system of claim 2, wherein the document data sequence does not include metadata associated with the document file.

4. The system of claim 1, wherein the first file comprises a source code file.

5. The system of claim 1, wherein to modify the security setting associated with the first file includes to increase an access restriction to the first file.

6. The system of claim 1, wherein in response to the determination that the data security policy is violated based at least in part on the determination that the first sketch and the second sketch at least partially overlap, the second one or more processors are further configured to send an alert to a device.

7. The system of claim 1, wherein in response to the determination that the data security policy is violated based at least in part on the determination that the first sketch and the second sketch at least partially overlap, the second one or more processors are further configured to increase an access restriction to the second file.

8. The system of claim 1, wherein in response to the determination that the data security policy is violated based at least in part on the determination that the first sketch and the second sketch at least partially overlap, the second one or more processors are further configured to modify a storage location associated with the at least one of the first file and the second file.

9. The system of claim 1, wherein the corresponding hash value comprises a first corresponding hash value, wherein the respective subset of hash values comprises a first respective subset of hash values, wherein a gene sequence associated with a third file, and wherein the second one or more processors are further configured to:
    apply the k-length sliding window to the gene sequence or each partition of the gene sequence and generate a second corresponding hash value for each sliding window;
    select a second respective subset of hash values associated with the gene sequence or each partition of the gene sequence;
    determine a third sketch based on the selected second respective subset of hash values associated with the gene sequence or each partition of the gene sequence; and
    send the third sketch associated with the gene sequence or each partition of the gene sequence over the network.

10. The system of claim 9, wherein the selected second respective subset of the hash values associated with the gene sequence or each partition of the gene sequence comprises a subset of smallest hash values.

11. The system of claim 9, wherein the keys comprising subsequences of hash values comprise first keys comprising first subsequences of hash values, wherein the key comprises a first key, wherein the second one or more processors are further configured to determine that the third sketch and a fourth sketch corresponding to a fourth file at least partially overlap comprises to:
    determine second keys comprising second subsequences of hash values;
    group the third sketch and the fourth sketch based on the third sketch and the fourth sketch both matching a second key;
    perform a pairwise comparison between the third sketch and the fourth sketch; and
    determine that the third sketch and the fourth sketch are related based at least in part on the pairwise comparison.

12. The system of claim 11, wherein the pairwise comparison comprises a determination of a Jaccard similarity coefficient between the third sketch and the fourth sketch.

13. The system of claim 11, wherein the second keys are determined by applying an M-hash value length sliding window to at least one of the third sketch and the fourth sketch.

14. The system of claim 11, wherein the first one or more processors are further configured to: in response to the determination that the third sketch and the fourth sketch are related, present a visual presentation describing that the third file and the fourth file are related.

15. A method, comprising:

applying, using first one or more processors, a k-length sliding window to a linguistic unit associated with a document data sequence to generate a corresponding hash value for each sliding window, wherein the document data sequence is associated with a first file;

selecting, using the first one or more processors, a respective subset of hash values associated with the linguistic unit;

determining, using the first one or more processors, a first sketch associated with the document data sequence based at least in part on the respective subset of hash values associated with the linguistic unit;

sending, using the first one or more processors, the first sketch associated with the document data sequence over a network;

receiving, over the network, the first sketch corresponding to the first file, wherein the first sketch was determined from hash values generated from a data sequence associated with the first file;

determining, using second one or more processors, that the first sketch and a second sketch corresponding to a second file at least partially overlap, wherein to determine that the first sketch and the second sketch corresponding to the second file at least partially overlap comprises:

determining keys comprising subsequences of hash values;

grouping the first sketch and the second sketch based on the first sketch and the second sketch both matching a key;

determining whether a count of matching sketches to the key meets or is greater than a threshold count; and in response to a determination that the count of the matching sketches to the key does not meet or exceed the threshold count, determining that the first sketch and the second sketch are related; and in response to a determination that a data security policy is violated based at least in part on the determination that the first sketch and the second sketch at least partially overlap, modifying a security setting associated with the first file.

16. A computer program product embodied in a non-transitory computer readable medium and comprising computer instructions for:

applying, using first one or more processors, a k-length sliding window to a linguistic unit associated with a document data sequence to generate a corresponding hash value for each sliding window, wherein the document data sequence is associated with a first file;

selecting, using the first one or more processors, a respective subset of hash values associated with the linguistic unit;

determining, using the first one or more processors, a first sketch associated with the document data sequence based at least in part on the respective subset of hash values associated with the linguistic unit; and sending, using the first one or more processors, the first sketch associated with the document data sequence over a network;

receiving, over the network, the first sketch corresponding to the first file, wherein the first sketch was determined from hash values generated from a data sequence associated with the first file;

determining, using second one or more processors, that the first sketch and a second sketch corresponding to a second file at least partially overlap, wherein to determine that the first sketch and the second sketch corresponding to the second file at least partially overlap comprises:

determining keys comprising subsequences of hash values;

grouping the first sketch and the second sketch based on the first sketch and the second sketch both matching a key;

determining whether a count of matching sketches to the key meets or is greater than a threshold count; and in response to a determination that the count of the matching sketches to the key does not meet or exceed the threshold count, determining that the first sketch and the second sketch are related; and in response to a determination that a data security policy is violated based at least in part on the determination that the first sketch and the second sketch at least partially overlap, modifying a security setting associated with the first file.

* * * * *